(12) United States Patent
Tanaka et al.

(10) Patent No.: US 10,815,233 B2
(45) Date of Patent: Oct. 27, 2020

(54) DIHYDROINDOLIZINONE DERIVATIVE

(71) Applicant: ONO PHARMACEUTICAL CO., LTD., Osaka (JP)

(72) Inventors: Motoyuki Tanaka, Osaka (JP); Takashi Kondo, Osaka (JP); Yasuo Hirooka, Osaka (JP); Taihei Nishiyama, Osaka (JP); Atsushi Hiramatsu, Osaka (JP); Tomoyuki Koda, Osaka (JP); Sho Kouyama, Osaka (JP)

(73) Assignee: ONO PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 16/720,486

(22) Filed: Dec. 19, 2019

(65) Prior Publication Data

US 2020/0140435 A1  May 7, 2020

Related U.S. Application Data

(60) Division of application No. 16/527,489, filed on Jul. 31, 2019, now Pat. No. 10,550,119, which is a division of application No. 16/050,266, filed on Jul. 31, 2018, now Pat. No. 10,407,426, which is a continuation of application No. 15/534,247, filed as application No. PCT/JP2015/084573 on Dec. 9, 2015, now Pat. No. 10,065,955.

(30) Foreign Application Priority Data

| Dec. 10, 2014 | (JP) | 2014-249822 |
| Dec. 25, 2014 | (JP) | 2014-263251 |
| Mar. 9, 2015 | (JP) | 2015-046150 |
| Aug. 17, 2015 | (JP) | 2015-160632 |

(51) Int. Cl.
| *C07D 471/04* | (2006.01) |
| *C07D 401/14* | (2006.01) |
| *C07D 487/04* | (2006.01) |
| *A61P 43/00* | (2006.01) |
| *A61K 9/20* | (2006.01) |
| *A61K 31/519* | (2006.01) |
| *A61K 31/444* | (2006.01) |

(52) U.S. Cl.
CPC .......... *C07D 471/04* (2013.01); *A61K 9/20* (2013.01); *A61K 31/444* (2013.01); *A61K 31/519* (2013.01); *A61P 43/00* (2018.01); *C07D 401/14* (2013.01); *C07D 487/04* (2013.01)

(58) Field of Classification Search
CPC ...... A61K 31/444; A61K 31/519; A61K 9/20; A61P 43/00; C07D 401/14; C07D 471/04; C07D 487/04
See application file for complete search history.

(56) References Cited

U.S. PATENT DOCUMENTS

2009/0176812 A1  7/2009  Kuroita et al.

FOREIGN PATENT DOCUMENTS

| DE | 44 07 488 | 9/1995 |
| EP | 0 407 342 | 1/1991 |
| EP | 1 506 967 | 2/2005 |
| JP | 5-255258 | 10/1993 |
| JP | 2010-510962 | 4/2010 |
| WO | 03/068230 | 8/2003 |
| WO | 2006/030032 | 3/2006 |
| WO | 2007/070826 | 6/2007 |
| WO | 2008/076805 | 6/2008 |
| WO | 2009/076337 | 6/2009 |
| WO | 2012/046882 | 4/2012 |
| WO | 2013/093484 | 6/2013 |
| WO | WO 2013/093484 | * 6/2013 ........... C07D 401/14 |
| WO | 2015/120777 | 8/2015 |

OTHER PUBLICATIONS

International Search Report dated Jan. 12, 2016 in International (PCT) Application No. PCT/JP2015/084573.
International Search Report and Written Opinion of the International Searching Authority dated Feb. 27, 2013 in International (PCT) Application No. PCT/GB2012/053217.
International Preliminary Report on Patentability dated Jul. 3, 2014 in International (PCT) Application No. PCT/GB2012/053217.
Search Report dated Apr. 19, 2012 in Application No. GB 1122139.7.
Office Action dated Sep. 9, 2016 in U.S. Appl. No. 14/366,396.
Office Action dated May 22, 2015 in European Application No. 12 813 423.6.
Notification of Reasons for Refusal translation dated Jan. 16, 2017 in Japanese Application No. 2014-548196, with English translation.
Patent Examination Report No. 1 dated Aug. 29, 2016 in Australian Application No. 2012356374.
Office Action dated May 6, 2015 in Chinese Application No. 201280070352.3, with English translation.
Office Action dated Mar. 17, 2017 in Indonesian Application No. P00201403648, with English translation.
First Examination Report dated Apr. 10, 2015 in New Zealand Application No. 626176.

(Continued)

*Primary Examiner* — Erich A Leeser
(74) *Attorney, Agent, or Firm* — Wenderoth, Lind & Ponack, L.L.P.

(57) ABSTRACT

A compound represented by general formula (I) (wherein all symbols are as defined in the description) or a salt, solvate, N-oxide form or prodrug thereof is a potent FXIa inhibitor, has excellent oral absorption properties and kinetics in blood, can exert a potent anti-coagulation activity over a long period of time after being administered orally, and has a discrepancy between the anti-coagulation activity thereof and the CYP-inhibiting activity thereof. Therefore, the compound or the salt, solvate, N-oxide form or prodrug thereof can be used as an efficient prophylactic and/or therapeutic agent for vascular occlusive diseases.

4 Claims, 2 Drawing Sheets

(56) References Cited

OTHER PUBLICATIONS

Invitation to Respond to Written Opinion dated Apr. 7, 2015 in Singapore Application No. 11201403402V.
Invitation to Respond to Written Opinion dated Nov. 2, 2015 in Singapore Application No. 11201403402V.
Examination Report dated Nov. 30, 2016 in Taiwanese Application No. 101148629.
Von dem Borne et al., "Factor XI enhances fibrin generation and inhibits fibrinolysis in a coagulation model initiated by surface-coated tissue factor", Blood Coagulation and Fibrinolysis, vol. 17, 2006, pp. 251-257.
Galiani et al., "Factor XI Activation in a Revised Model of Blood Coagulation", Science, vol. 253, Aug. 1991, pp. 909-912.
Gruber et al., "Factor XI-dependence of surface- and tissue factor-initiated thrombus propagation in primates", BLOOD, vol. 102, No. 3, Aug. 1, 2003, pp. 953-955.
Wang et al., "Effects of factor IX or factor XI deficiency on ferric chloride-induced carotid artery occlusion in mice", Journal of Thrombosis and Haemostasis, vol. 3, 2005, pp. 695-702.
Wang et al., "Effects of factor XI deficiency on ferric chloride-induced vena cava thrombosis in mice", Journal of Thrombosis and Haemostasis, vol. 4, 2006, pp. 1982-1988.
Younis et al., "Antisense inhibition of coagulation factor XI prolongs APTT without increased bleeding risk in cynomolgus monkeys", Blood, vol. 119, No. 10, Mar. 2012, pp. 2401-2408.
Tucker et al., "Prevention of vascular graft occlusion and thrombus-associated thrombin generation by inhibition of factor XI", Blood, vol. 113, No. 4, Jan. 2009, pp. 936-944.
Yamashita et al., "Factor XI contributes to thrombus propagation on injured neointima of the rabbit iliac artery", Journal of Thrombosis and Haemostasis, vol. 4, 2006, pp. 1496-1501.
Al-Horani et al., "Factor X1A inhibitors: A review of the patent literature", Expert Opinion on Therapeutic Patents, vol. 26, No. 3, 2016, pp. 323-345.
Huebsch et al., "Preparation of (biphenylmethyl)pyridone and (pyridylmethyl) pyridone pharmaceuticals for the treatment of glaucoma", DE 44 07 488, Caplus Accession No. 124:87020, 1995.
Horig et al., "From bench to clinic and back: Perspective on the 1st IQPC Translational Research conference", Journal of Translational Medicine, vol. 2, No. 44, 2004, 8 pages.
Ito et al., "A medium-term rat liver bioassay for rapid in vivo detection of carcinogenic potential of chemicals", Cancer Sci., vol. 94, No. 1, Jan. 2003, pp. 3-8.
Schafer et al., "Failure is an option: learning from unsuccessful proof-of-concept trials", Drug Discovery Today, vol. 13, Nos. 21-22, Nov. 2008, pp. 913-916.
Wong et al., "A small-molecule factor XIa inhibitor produces antithrombotic efficacy with minimal bleeding time prolongation in rabbits", J Thromb Thrombolysis, vol. 32, 2011, pp. 129-137.
Wolff, Manfred E., Burger's Medicinal Chemistry and Drug Discovery, Fifth Ed., vol. 1: Principles and Practice, John Wiley & Sons, 1995, 975.
Banker, Gilbert S. et al., Modern Pharmaceutics, Marcel Dekker, New York, 1996.
West, Anthony R., Solid State Chemistry and Its Applications, Wiley, New York, 1988, 358.
Office Action dated Nov. 28, 2018 in corresponding U.S. Appl. No. 15/644,655.
Paluchowska et al., "Novel N-{w-[4-(2-methoxyphenyl)piperazin-1-yl)-ethyl}pyrid-2(1H)-ones with Diversified 5-$HT_{1A}$ receptor activity", Polish Journal of Pharmacology, vol. 54, Oct. 14, 2002, pp. 641-646.

\* cited by examiner

DIHYDROINDOLIZINONE DERIVATIVE

TECHNICAL FIELD

The present invention relates to a compound represented by general formula (I):

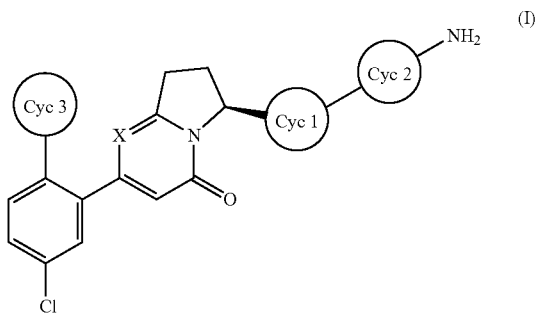

(wherein, all the symbols have the same meanings as described below), a salt thereof, a solvate thereof, an N-oxide thereof or a prodrug thereof (hereinafter occasionally abbreviated as the compound of the present invention).

BACKGROUND ART

Thrombosis and thromboembolism which is a complication of thrombosis (hereinafter referred to as thromboembolic disease) are ranked high along with cancer as the cause of death of adults, and have become important problems in recent years. Thromboembolic disease occurs by the formation of a thrombus at a site of vascular injury. Alternatively, thromboembolic disease occurs when a thrombus is released and is carried by the blood stream into another blood vessel where the thrombus obstructs a blood vessel at another site. Thromboembolic disease includes, for example, venous thromboembolism which is a collective term for deep venous thrombosis and pulmonary embolism, cerebral stroke, angina pectoris, myocardial infarction, other various arterial and venous thrombosis and the like.

Tissue factor expressed on a vascular wall due to the injury of a blood vessel and the like becomes the starting point of the blood coagulation cascade and forms a complex with blood coagulation factor VII which is present in blood in a very small quantity. This complex activates blood coagulation factor IX and blood coagulation factor X, and activated blood coagulation factor X converts prothrombin to thrombin. Thrombin converts fibrinogen to fibrin and finally insoluble fibrin is formed (the initial stage). It is supposed that thrombin produced in the process promotes the formation of a thrombus at the initial stage and is important for hemostasis. On the other hand, it has been reported that thrombin activates blood coagulation factor XI and causes explosive thrombin production via activated blood coagulation factor XI (hereinafter also referred to as FXIa) (the amplification stage), which results in an increase in thrombi (see Non Patent Literatures 1 to 3).

For the treatment and/or prevention of thromboembolic disease, anticoagulant agents are generally used. Though conventional anticoagulant agents exhibit excellent antithrombotic actions, bleeding complications, which are serious side effects, have been problematic. Alternatively, in order not to cause bleeding complications, the doses of the agents are limited and it is supposed that there is a possibility that the agents do not exhibit sufficient antithrombotic actions. Under such conditions, an agent for treating and/or preventing thrombosis and thromboembolism having a novel mechanism of action, which suppresses the growth of or increase in pathological thrombi and does not affect the formation of hemostatic thrombi, is required. As one of the targets of the agent, FXIa is attracting attention in recent years. Blood coagulation factor XI is one of plasma serine proteases which are involved in the regulation of blood coagulation and becomes FXIa by activated blood coagulation factor XII, thrombin or itself. FXIa is one of constituents of the blood coagulation pathway which is referred to as the intrinsic system or the contact system in the classical blood coagulation cascade and activates blood coagulation factor IX by selectively cleaving peptide bonds of Arg-Ala and Arg-Val. The safety of FXIa is supported by the observations that the blood coagulation factor XI deficiency in humans, which is called hemophilia C, results in mild to moderate bleeding characterized primarily by postoperative or posttraumatic hemorrhage. In addition, the effects and the high safety of FXIa are demonstrated by the experimental results of experimental thrombosis and bleeding models which used blood coagulation factor XI deficient mice and the experimental results of an anti-blood coagulation factor XI neutralizing antibody or an antisense in experimental thrombosis and bleeding models which used monkeys or rabbits, in addition to the results of observations of the blood coagulation factor XI deficiency in humans (see Non Patent Literatures 4 to 8).

Based on the above results, it is expected that FXIa is a very attractive target without exhibiting the side effect of bleeding when developing an antithrombotic agent for treatment and/or prevention and an FXIa inhibitor becomes a very potent and safe antithrombotic agent for treatment or prevention without having any undesirable side effects such as bleeding.

Incidentally, as compounds of prior arts to the present invention, the following compounds are described:

It has been described in Patent Literature 1 that a compound represented by general formula (A):

(wherein, $A^A$ represents a 5- to 12-membered heterocycle or the like; $L_{1A}$ represents —CH=CH— or the like; $R^{11A}$ represents benzyl or the like; and $M^A$ represents imidazolyl or the like) is useful as a selective inhibitor of FXIa or a dual inhibitor of FXIa and plasma kallikrein.

In addition, it has been described in Patent Literature 2 that a compound represented by general formula (B-I):

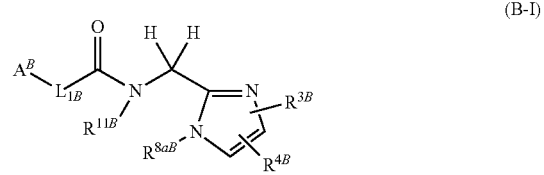

(wherein, $A^B$ represents a 5- to 12-membered heterocycle or the like; $L_{1B}$ represents —CH=CH— or the like; $R^{11B}$ represents benzyl or the like; $R^{3B}$ represents phenyl or the like; $R^{4B}$ represents chlorine or the like; $R^{8aB}$ represents hydrogen or the like); or general formula (B-II):

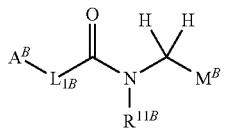
(B-II)

(wherein, $M^B$ represents pyridyl or the like; and the other symbols have the same meanings as described above) inhibits FXIa and/or plasma kallikrein.

Further, it has been described in Patent Literature 3 that a compound represented by general formula (C):

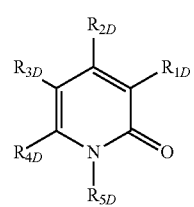
(C)

(wherein, $W^C$ represents CO or the like; $G^C$ represents a direct bond or the like; $G^{1C}$, $G^{2C}$, $G^{3C}$ and $G^{4C}$ each independently represent C or N or the like; $R^{9C}$ represents an aryl or the like; $R^{10C}$ represents a heteroaryl or the like; and $R^{14C}$ represents a heteroarylalkyl or the like) is useful as a γ secretase modulator. However, it is not reported that the compound represented by formula (C) has an FXIa inhibitory activity.

Furthermore, it has been described in Patent Literature 4 that a compound represented by general formula (D):

(D)

(wherein, $R_{1D}$ represents hydrogen or the like; $R_{2D}$ represents an aryl or the like; $R_{3D}$ represents hydrogen or the like; $R_{4D}$ represents hydrogen or the like; and $R_{5D}$ represents a heteroarylalkyl or the like) is useful as a p38 MAP kinase modulator.

In addition, it has been described in Patent Literature 5 that a compound represented by general formula (E):

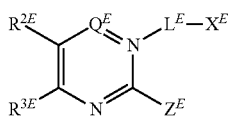
(E)

(wherein, $L^E$ represents a linker providing 0 to 6 atoms or the like; $X^E$ represents a heteroaryl or the like; $Z^E$ represents a halogen or the like; $Q^E$ represents CO or the like; and $R^{2E}$ and $R^{3E}$ each independently represent hydrogen, an aryl or the like) is useful as a dipeptidyl peptidase inhibitor.

Further, it has been described in Patent Literature 6 that a compound represented by general formula (F):

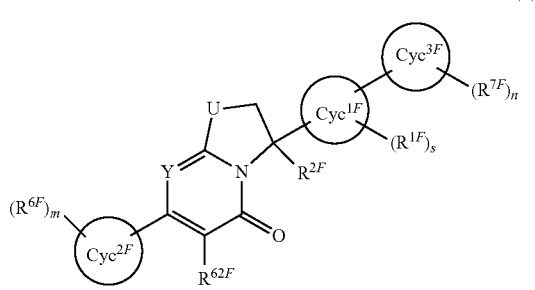
(F)

(wherein, $Cyc^{1F}$ represents a 5- to 10-membered heteroaryl or the like, $Cyc^{2F}$ represents a C5-C10 aryl or the like, $Cyc^{3F}$ represents a C5-C10 aryl or a 5- to 10-membered heteroaryl or the like, U represents $CH_2$ or the like, Y represents N or $C(R^{5F})$ or the like, and $R^{6F}$ represents a 5- to 10-membered heteroaryl or the like) is useful as a selective inhibitor of FXIa or a dual inhibitor of FXIa and plasma kallikrein.

However, none of literature specifically discloses the compound of the present invention.

CITATIONS LISTS

Patent Literatures

Patent Literature 1: WO 2007070826 A
Patent Literature 2: WO 2008076805 A
Patent Literature 3: WO 2009076337 A
Patent Literature 4: WO 2003068230 A
Patent Literature 5: EP 1 506 967 A1
Patent Literature 6: WO 2013093484 A Non Patent Literatures Non Patent Literature 1: Blood Coagulation and Fibrinolysis, 2006, Vol. 17, pages 251-257
Non Patent Literature 2: Science, 1991, Vol. 253, pages 909-912
Non Patent Literature 3: Blood, 2003, Vol. 102, pages 953-955
Non Patent Literature 4: Journal of Thrombosis and Haemostasis, 2005, Vol. 3, pages 695-702
Non Patent Literature 5: Journal of Thrombosis and Haemostasis, 2006, Vol. 4, pages 1982-1988
Non Patent Literature 6: Blood, 2012, Vol. 119, pages 2401-2408
Non Patent Literature 7: Blood, 2009, Vol. 113, pages 936-944
Non Patent Literature 8: Journal of Thrombosis and Haemostasis, 2006, Vol. 4, pages 1496-1501

SUMMARY OF INVENTION

Technical Problems

An object of the present invention is to develop a compound which is a potent FXIa inhibitor, is excellent in oral absorbability and kinetics in blood, exhibits a potent anticoagulation activity for a long period of time after oral administration and has a discrepancy between the anticoagulation activity and a CYP inhibitory activity.

Solutions to Problems

The present inventors have carried out intensive studies in order to achieve the above-described object. As a result, the present inventors have found that the compound of the present invention is capable of achieving the above-described object, and have completed the present invention.

In other words, the present invention relates to the followings:

[1] A compound represented by general formula (I):

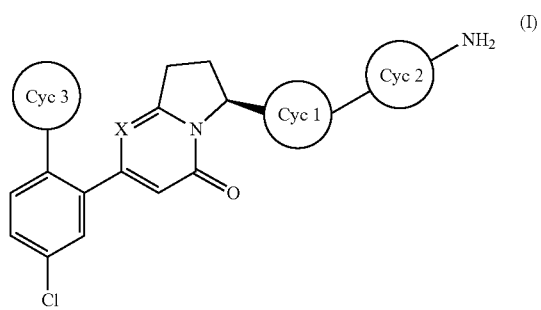

[wherein,

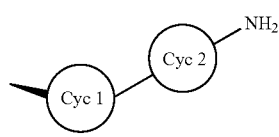

represents:

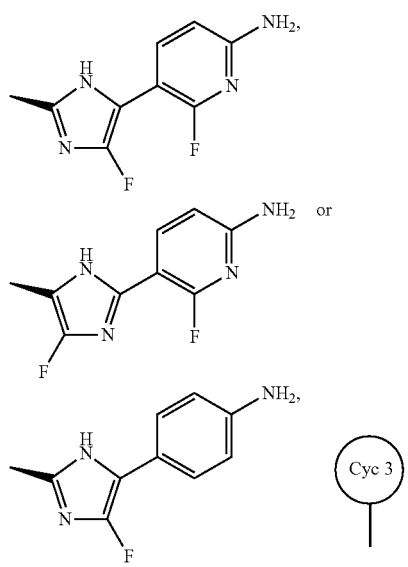

represents:

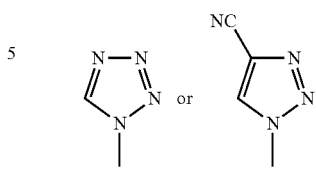

or
and X represents CH or N];
a salt thereof, a solvate thereof, an N-oxide thereof or a prodrug thereof;

[2] the compound according to the above item [1], wherein the compound represented by general formula (I) is (3S)-3-[5-(6-amino-2-fluoro-3-pyridinyl)-4-fluoro-1H-imidazol-2-yl]-7-[5-chloro-2-(1H-tetrazol-1-yl)phenyl]-2,3-dihydro-5(1H)-indolizinone, a salt thereof, a solvate thereof, an N-oxide thereof or a prodrug thereof;

[3] the compound according to the above item [1], wherein the compound represented by general formula (I) is (3S)-3-[2-(6-amino-2-fluoro-3-pyridinyl)-4-fluoro-1H-imidazol-5-yl]-7-[5-chloro-2-(1H-tetrazol-1-yl)phenyl]-2,3-dihydro-5(1H)-indolizinone, a salt thereof, a solvate thereof, an N-oxide thereof or a prodrug thereof;

[4] the compound according to the above item [1], wherein the compound represented by general formula (I) is (6S)-6-[2-(6-amino-2-fluoro-3-pyridinyl)-4-fluoro-1H-imidazol-5-yl]-2-[5-chloro-2-(1H-tetrazol-1-yl)phenyl]-7,8-dihydropyrrolo[1,2-a]pyrimidin-4(6H)-one, a salt thereof, a solvate thereof, an N-oxide thereof or a prodrug thereof;

[5] the compound according to the above item [1], wherein the compound represented by general formula (I) is 1-(2-{(3S)-3-[5-(4-aminophenyl)-4-fluoro-1H-imidazol-2-yl]-5-oxo-1,2,3,5-tetrahydro-7-indolizinyl}-4-chlorophenyl)-1H-1,2,3-triazole-4-carbonitrile, a salt thereof, a solvate thereof, an N-oxide thereof or a prodrug thereof;

[6] a pharmaceutical composition comprising the compound according to any one of the above items [1] to [5], a salt thereof, a solvate thereof, an N-oxide thereof or a prodrug thereof as an active ingredient;

[7] an FXIa inhibitor comprising the compound according to any one of the above items [1] to [5], a salt thereof, a solvate thereof, an N-oxide thereof or a prodrug thereof as an active ingredient;

[8] an agent for preventing and/or treating thromboembolic disease, comprising the compound according to any one of the above items [1] to [5], a salt thereof, a solvate thereof, an N-oxide thereof or a prodrug thereof as an active ingredient;

[9] the agent according to the above item [8], wherein the thromboembolic disease is arterial cardiovascular thromboembolic disorder, venous cardiovascular thromboembolic disorder, arterial cerebrovascular thromboembolic disorder, venous cerebrovascular thromboembolic disorder or thromboembolic disorder in the heart chamber or in the peripheral circulation;

[10] the agent according to the above item [8] or [9], wherein the thromboembolic disease is coronary artery disease, unstable angina, acute coronary syndrome, atrial fibrillation, myocardial infarction, ischemic sudden death, transient ischemic attack, cerebral stroke, peripheral arterial disease, atherosclerosis, peripheral occlusive arterial disease, venous thrombosis, venous thromboembolism, deep venous thrombosis, thrombophlebitis, arterial embolism, coronary artery thrombosis, cerebral arterial thrombosis, cerebral embolism, kidney embolism, portal vein thrombosis, pulmonary embolism, pulmonary infarction, liver embolism, hepatic veno-occlusive disease/sinusoidal obstruction syndrome, thrombotic microangiopathy, disseminated intravascular coagulation, sepsis, acute respiratory distress syndrome, acute lung injury, antiphospholipid antibody syndrome, thrombosis resulting from coronary artery bypass graft surgery or thrombosis induced by treatment in which blood is exposed to an artificial surface which promotes thrombus formation;

[11] the agent according to any one of the above items [8] to [10], wherein the thromboembolic disease is venous thromboembolism, ischemic stroke, thromboembolic disease induced by treatment in which blood is exposed to an artificial surface which promotes thrombus formation, acute coronary syndrome, coronary artery disease or peripheral arterial disease;

[12] the compound according to any one of the above items [1] to [5], a salt thereof, a solvate thereof, an N-oxide thereof or a prodrug thereof for preventing and/or treating thromboembolic disease;

[13] use of the compound according to any one of the above items [1] to [5], a salt thereof, a solvate thereof, an N-oxide thereof or a prodrug thereof for manufacture of an agent for preventing and/or treating thromboembolic disease; and

[14] a method for preventing and/or treating thromboembolic disease, comprising administering an effective dose of the compound according to any one of the above items [1] to [5], a salt thereof, a solvate thereof, an N-oxide thereof or a prodrug thereof to a patient in need of prevention and/or treatment of the thromboembolic disease;

and the like.

Advantageous Effects of Invention

The compound of the present invention is a potent FXIa inhibitor, and therefore, is an effective agent for preventing and/or treating thromboembolic disease.

DESCRIPTION OF EMBODIMENTS

Figure 1:
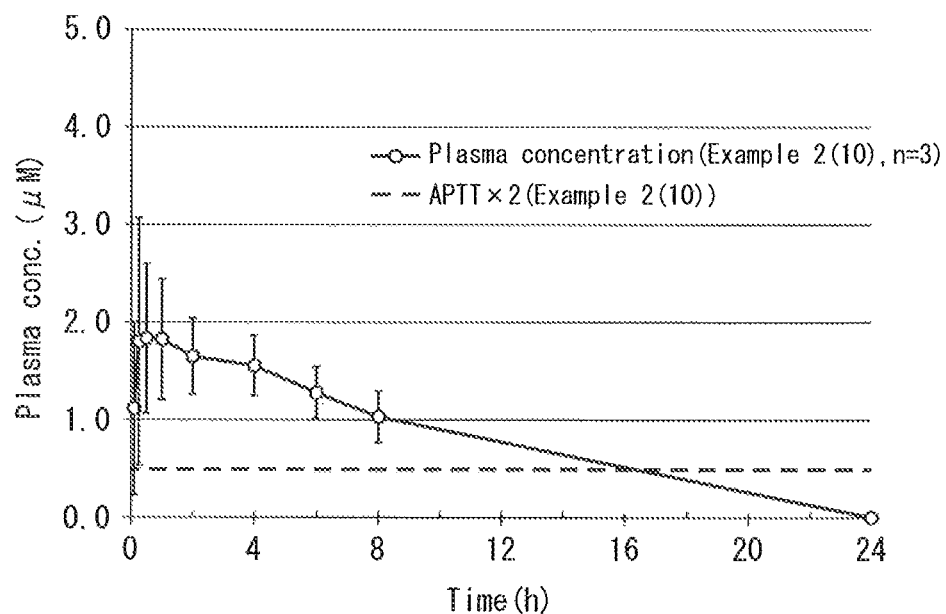
FIG. 1 shows the change in the concentration of the compound in the plasma of the compound described in Example 2 (10) when being orally administered to rats (1 mg/kg) and the relationship to APTT×2 in an in vitro assay. The longitudinal axis shows the concentration of the compound in the plasma and the horizontal axis shows time after oral administration.

The present invention will be described in details hereinbelow.

In the present invention, unless otherwise specified, the symbol:

represents that a substituent binds to the back side on the paper surface (in other words, α-configuration), the symbol:

represents that a substituent binds to the front side on the paper surface (in other words, α-configuration), and the symbol:

represents an arbitrary mixture of α-configuration and β-configuration, as would be apparent to those skilled in the art.

Unless otherwise specifically indicated, all isomers are included in the present invention. For example, an alkyl group includes linear and branched ones. In addition, all of isomers due to the presence of asymmetric carbon(s) and the like (R-, S-, α- and β-configurations, enantiomer(s) and diastereomer(s)), optically active substances having optical rotation (D-, L-, d- and l-forms), polar substances by chromatographic separation (more polar and less polar substances), compounds in equilibrium (for example, tautomers due to an amide bond and the like), rotational isomers, a mixture thereof in any proportion and a racemic mixture are included in the present invention.

Further, optical isomers in the present invention may include, not only 100%-pure isomers, but also less than 50%-pure optical isomers.

The compound of the present invention can be converted into a corresponding salt by a known method. The salt is preferably a pharmaceutically acceptable salt and is more preferably a water-soluble salt. Examples of the appropriate salt include an acid addition salt (such as a salt of an inorganic acid, for example, a hydrochloride, a hydrobromide, a hydroiodide, a sulfate, a phosphate and a nitrate as well as a salt of an organic acid, for example, an acetate, a lactate, a tartrate, a benzoate, a citrate, a methanesulfonate, an ethanesulfonate, a benzenesulfonate, a toluenesulfonate, an isethionate, a glucuronate and a gluconate), a salt of an alkali metal (such as potassium and sodium), a salt of an alkaline earth metal (such as calcium and magnesium), an ammonium salt or a salt of a pharmaceutically acceptable organic amine (such as tetramethylammonium, triethylamine, methylamine, dimethylamine, cyclopentylamine, benzylamine, phenethylamine, piperidine, monoethanolamine, diethanolamine, tris(hydroxymethyl)aminomethane, lysine, arginine and N-methyl-D-glucamine) and the like.

The compound of the present invention or a salt thereof can be also converted into a solvate. The solvate is preferably a low-toxicity and water-soluble solvate. Examples of the appropriate solvate include a solvate of water and a solvate of an alcohol based solvent (such as a solvate of ethanol).

An N-oxide of the compound of the present invention represents a compound obtained by oxidation of a nitrogen atom in the compound of the present invention. In addition, the N-oxide of the compound of the present invention may be further converted to the above-described alkaline (alkaline earth) metal salt, the ammonium salt, the organic amine salt or the acid addition salt.

In addition, a prodrug of the compound of the present invention refers to a compound which is converted to the compound of the present invention by a reaction caused by an enzyme, gastric acid and the like in vivo. Specifically, examples of the prodrug of the compound of the present invention include a compound obtained by making an amino group of the compound of the present invention be eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, acetoxymethylated, tert-butylated and the like. These compounds can be prepared by a known method. In addition, the prodrug of the compound of the present invention may be either a hydrate or a non-hydrate. Further, the prodrug of the compound of the present invention may be a compound which is converted to the compound of the present invention under a physiological condition as described in "Iyakuhin no kaihatsu (Pharmaceutical research and development)", Vol. 7, "Bunshi sekkei (Molecular Design)", pages 163-198, Hirokawa-Shoten Ltd., published 1990.

Furthermore, each atom constituting the compound of the present invention may also be replaced by an isotope (such as $^2$H, $^3$H, $^{13}$C, $^{14}$C, $^{15}$N, $^{16}$N, $^{17}$O, $^{18}$O, $^{35}$S, $^{36}$Cl, $^{77}$Br and $^{125}$I) and the like.

The compound of the present invention can form a pharmaceutically acceptable cocrystal or cocrystalline salt. In this regard, the cocrystal or cocrystalline salt means a crystalline material which is constituted by two or more kinds of unique solids at room temperature each having different physical characteristics (for example, the structure, the melting point, the heat of fusion, the hygroscopic property, the solubility, the stability and the like). The cocrystal or cocrystalline salt can be prepared by a known method for cocrystallization per se.

[Processes for the Preparation of the Compound of the Present Invention]

The compound of the present invention can be prepared by a known method. For example, the compound of the present invention can be prepared by appropriately improving and combining the methods described hereinbelow, the methods described in Examples or the method described in Comprehensive Organic Transformations: A Guide to Functional Group Preparations 2nd Edition (Richard C. Larock, John Wiley & Sons Inc., 1999 and the like.

[Toxicity]

The toxicity of the compound of the present invention is sufficiently low, and the compound of the present invention can be used as a pharmaceutical safely.

[Application to Pharmaceuticals]

The compound of the present invention has a potent FXIa inhibitory activity. Accordingly, the compound of the present invention is useful for preventing and/or treating thromboembolic disease, for example, arterial cardiovascular thromboembolic disorder, venous cardiovascular thromboembolic disorder, arterial cerebrovascular thromboembolic disorder, venous cerebrovascular thromboembolic disorder and thromboembolic disorder in the heart chamber or in the peripheral circulation.

Examples of the arterial cardiovascular thromboembolic disorder include coronary artery disease, ischemic cardiomyopathy, acute coronary syndrome, coronary artery thrombosis, ischemic complications of unstable angina and non-Q wave myocardial infraction, ST-segment elevation and/or non ST-segment elevation acute myocardial infarction which is medically cared or involves percutaneous coronary intervention, angina pectoris such as stable (exercise-induced) angina pectoris, variant angina pectoris, unstable angina, myocardial infarction (such as initial myocardial infarction and recurrent myocardial infarction), acute myocardial infarction, reocclusion and stenosis of a blood vessel after coronary artery bypass graft surgery, reocclusion and stenosis after percutaneous transluminal angioplasty, cardiac/transcoronary stent implantation and after thrombolytic therapy for coronary artery, ischemic sudden death and the like.

Examples of the venous cardiovascular thromboembolic disease include deep venous thrombosis (DVT) and/or pulmonary embolism (PE) in major general surgery, abdominal surgery, hip replacement arthroplasty, knee replacement arthroplasty, hip fracture surgery, multiple bone fracture, multiple trauma, traumatic injury, spinal cord injury, burn injury or at the time of entering critical care unit, DVT and/or PE in a patient with acute medical disease with a significantly limited physical activity, DVT and/or PE in a patient receiving cancer chemotherapy, DVT and/or PE in a patient with cerebral stroke, symptomatic or asymptomatic DVT regardless of the presence/absence of PE and the like.

Examples of the arterial cerebrovascular thromboembolic disorder include cerebral stroke, ischemic stroke, the acute phase of cerebral infarction, cerebral stroke in a patient with nonvalvular atrial fibrillation or valvular atrial fibrillation, cerebral arterial thrombosis, cerebral infarction, transient ischemic attack (TIA), lacunar infarct, atherothrombotic cerebral infarction, cerebral arterial embolism, cerebral thrombosis, cerebrovascular disorder, asymptomatic cerebral infarction, vascular dementia and the like.

Examples of the venous cerebrovascular thromboembolic disorder include intracranial venous thrombosis, cerebral embolism, cerebral thrombosis, cerebral venous sinus thrombosis, intracranial venous sinus thrombosis, cavernous sinus thrombosis and the like.

Examples of the thromboembolic disease in the heart chamber or in the peripheral circulation include venous thrombosis, systemic venous thromboembolism, recurrent venous thromboembolism, thrombophlebitis, nonvalvular and valvular atrial fibrillation, cardiogenic embolism, disseminated intravascular coagulation (DIC), sepsis, acute respiratory distress syndrome (ARDS), acute lung injury (ALI), chronic obstructive pulmonary disease, antiphospholipid antibody syndrome, liver embolism, hepatic veno-occlusive disease (VOD), kidney embolism, renal vein thrombosis, renal artery occlusion, refractory nephrotic syndrome due to membranous nephropathy or focal sclerosing glomerulonephritis, splenic vein thrombosis, superior mesenteric arterial occlusion, portal vein thrombosis, retinal vein occlusion, atherosclerosis, atherothrombosis, peripheral arterial occlusive disease (PAOD), peripheral arterial disease, arterial embolism, diabetes and metabolic syndrome as well as sequelae thereof, thrombosis induced by the treatment in which blood is exposed to an artificial surface (such as a medical implant, a medical device, a catheter, a stent, a prosthetic cardiac valve and a hemodialyzer) which promotes thrombus formation and the like.

Preferable examples of the thromboembolic disease include coronary artery disease, unstable angina, acute coronary syndrome, atrial fibrillation, myocardial infarction (such as initial myocardial infarction and recurrent myocardial infarction), ischemic sudden death, transient ischemic attack, cerebral stroke, peripheral arterial disease, atherosclerosis, peripheral occlusive arterial disease, venous thrombosis, venous thromboembolism, deep venous thrombosis, thrombophlebitis, arterial embolism, coronary artery thrombosis, cerebral arterial thrombosis, cerebral embolism, kidney embolism, portal vein thrombosis, pulmonary embolism, pulmonary infarction, liver embolism, hepatic veno-occlusive disease (VOD)/sinusoidal obstruction syndrome (SOS), thrombotic microangiopathy (TMA), disseminated intravascular coagulation (DIC), sepsis, acute respiratory distress syndrome (ARDS), acute lung injury (ALI), antiphospholipid antibody syndrome, thrombosis due to coronary artery bypass graft surgery, thrombosis induced by the treatment in which blood is exposed to an artificial surface (such as a medical implant, a medical device, a catheter, a stent, a prosthetic cardiac valve and a hemodialyzer) which promotes thrombus formation and the like.

In the present specification, atrial fibrillation, atherosclerosis or sepsis includes thromboembolic disease induced by atrial fibrillation, atherosclerosis or sepsis.

More preferable examples of the thromboembolic disease include venous thromboembolism (VTE), ischemic stroke, thromboembolic disease induced by the treatment in which blood is exposed to an artificial surface which promotes thrombus formation, acute coronary syndrome, coronary artery disease, peripheral arterial disease and the like.

The venous thromboembolism (VTE) includes deep venous thrombosis (DVT), pulmonary embolism (PE) and pulmonary embolism which involves deep venous thrombosis. The prevention and/or treatment of the VTE includes the onset inhibition of VTE in a patient receiving an orthopedic surgery of lower extremity (such as total knee replacement arthroplasty, total hip replacement and operation of hip fracture), the onset inhibition of DVT and/or PE in a patient with acute medical disease with a significantly limited physical activity, the intraoperative and/or postoperative onset inhibition of VTE in a patient receiving abdominal surgery and the onset inhibition of DVT and/or PE in a patient receiving cancer chemotherapy.

The prevention and/or treatment of the ischemic stroke includes the onset inhibition of ischemic stroke and systemic embolism in a patient with nonvalvular atrial fibrillation, the onset inhibition of recurrent cerebral stroke and systemic embolism in a patient with embolic stroke of undetermined source (ESUS), the onset inhibition of ischemic stroke and systemic embolism in a patient with atrial fibrillation associated with acute coronary syndrome (ACS), the onset inhibition of ischemic stroke and systemic embolism in a patient with atrial fibrillation with chronic kidney disease (CKD) or end-stage renal disease and the inhibition of recurrence of ischemic stroke (excepting cardiogenic embolism).

The prevention and/or treatment of the thromboembolic disease induced by the treatment in which blood is exposed to an artificial surface which promotes thrombus formation includes the prevention and/or treatment of thromboembolic disease in a patient receiving prosthetic replacement, the prevention and/or treatment of thromboembolic disease in a patient with installation of a ventricular assist device such as an implantable ventricular assist device, a total replacement type ventricular assist device, a percutaneous ventricular assist device and an extracorporeal ventricular assist device and the prevention and/or treatment of thromboembolic disease in a patient with an indwelled coronary artery stent.

The prevention and/or treatment of the acute coronary syndrome (ACS), coronary artery disease or peripheral arterial disease includes the inhibition of a cardiovascular event in a patient with acute coronary syndrome (ACS), the inhibition of a cardiovascular event in a patient with coronary artery disease or peripheral arterial disease and the inhibition of a cardiovascular event in a patient with diabetes with a high cardiovascular risk (more preferably, in a patient with type 2 diabetes).

In addition, the compound of the present invention has a plasma kallikrein inhibitory action, and therefore, is useful for preventing and/or treating disease associated with plasma kallikrein.

Examples of the disease associated with plasma kallikrein include retinopathy, diabetic retinopathy, hypertensive retinopathy, proliferative and nonproliferative retinopathy, age-related macular degeneration (AMD), disorder related to the prevention and/or treatment of hematoma or increased vascular permeability, disease related to edema, hereditary angioedema (HAE), diabetic macular edema (DME), clinically significant macular edema (CSME), cystoid macular edema (CME), retinal edema, edema related to neuroglia, cerebral edema, lymphedema, angioedema, traumatic brain injury, hemorrhagic stroke, intracerebral hemorrhage, cerebral aneurysm, arteriovenous malformation, spinal cord injury, ischemia-reperfusion injury, ischemia, cerebral ischemia, pain, disorder accompanied with elements of inflammation, encephalitis, multiple sclerosis, pruritus, arthritis, inflammatory bowel disease, gout, psoriasis, disease related to activation of stellate cells, Alzheimer's disease, Parkinson's disease, amyotrophic lateral sclerosis, Creutzfeldt-Jakob disease, epilepsy, essential hypertension, hypertension related to diabetes or hyperlipidemia, renal failure, chronic kidney disease, heart failure, proteinuria, blood loss during surgery and the like.

Preferable examples of the disease associated with plasma kallikrein include disease related to edema, hereditary angioedema, macular edema, cerebral edema, retinopathy, formation of edema related to ischemia-reperfusion injury as well as blood loss during surgery such as cardiopulmonary bypass and coronary artery bypass grafting.

When the compound of the present invention is applied to a pharmaceutical, the compound of the present invention may be used not only as a single agent, but also as a combined medicine by being combined with other active ingredient(s), for example, agent(s) and the like which are listed hereinbelow for the purpose, for example, of:

(1) complementation and/or enhancement of the effects of preventing, treating and/or ameliorating symptoms, (2) improvement in the kinetics or absorption, and reduction of the dose, and/or (3) reduction of the side effects.

When the compound of the present invention is used for preventing and/or treating thromboembolic disease, examples of combined agent(s) which is used in combination with the compound of the present invention include an anticoagulant agent, an antiplatelet agent, a thrombolytic agent, a fibrinolytic agent, a serine protease inhibitor, an elastase inhibitor, a steroid, a combination thereof and the like.

Examples of the anticoagulant agent include a thrombin inhibitor, an antithrombin III activator, a heparin cofactor II activator, other FXIa inhibitors, a plasma and/or tissue kallikrein inhibitor, an inhibitor of plasminogen activator inhibitor (PAI-1), an inhibitor of thrombin-activatable fibrinolysis inhibitor (TAFI), a factor VIIa inhibitor, a factor VIIIa inhibitor, a factor IXa inhibitor, a factor Xa inhibitor, a factor XIIa inhibitor, a combination thereof and the like.

Examples of the antiplatelet agent include a GPII/IIIa blocker, a protease-activated receptor (PAR-1) antagonist, a PAR-4 antagonist, a phosphodiesterase III inhibitor, other phosphodiesterase inhibitors, a P2X1 antagonist, a P2Y1 receptor antagonist, a P2Y12 antagonist, a thromboxane receptor antagonist, a thromboxane A2 synthetase inhibitor, a cyclooxygenase-1 inhibitor, a phospholipase D1 inhibitor, a phospholipase D2 inhibitor, a phospholipase D inhibitor, a glycoprotein VI (GPVI) antagonist, a glycoprotein Ib (GPIB) antagonist, a GAS6 antagonist, aspirin, a combination thereof and the like.

Preferably, the combined agent is an antiplatelet agent.

Preferable examples of the antiplatelet agent include clopidogrel, prasugrel, ticagrelor, cangrelor, elinogrel, cilostazol, sarpogrelate, iloprost, beraprost, limaprost and/or aspirin, a combination thereof and the like.

Preferably, the combined agent is warfarin, unfractionated heparin, low-molecular-weight heparin, enoxaparin, dalteparin, bemiparin, tinzaparin, semuloparin sodium (AVE-5026), danaparoid, a synthesized pentasaccharide, fondaparinux, hirudin, disulfatohirudin, lepirudin, bivalirudin, desirudin, argatroban, aspirin, ibuprofen, naproxen, sulindac, indomethacin, mefenamate, droxicam, diclofenac, sulfinpyrazone, piroxicam, ticlopidine, clopidogrel, prasugrel, ticagrelor, cangrelor, elinogrel, cilostazol, sarpogrelate, iloprost, beraprost, limaprost, tirofiban, eptifibatide, abciximab, melagatran, ximelagatran, dabigatran, rivaroxaban, apixaban, edoxaban, darexaban, betrixaban, TAK-442, tissue plasminogen activator, a modified tissue plasminogen activator, anistreplase, urokinase, streptokinase, gabexate, gabexate mesilate, nafamostat, sivelestat, sivelestat sodium hydrate, alvelestat (AZD-9668), ZD-8321/0892, ICI-200880, human elafin (tiprelestat), elafin, a1-antitrypsin (A1AT), cortisone, betamethasone, dexamethasone, hydrocortisone, methylprednisolone, prednisolone, triamcinolone or a combination thereof.

In another embodiment, examples of the combined agent in the present invention include a potassium channel opener, a potassium channel blocker, a calcium channel blocker, an inhibitor of sodium-hydrogen exchanger, an antiarrhythmic agent, an antiarteriosclerotic agent, an anticoagulant agent, an antiplatelet agent, an antithrombotic agent, a thrombolytic agent, a fibrinogen antagonist, an antihypertensive diuretic, an ATPase inhibitor, a mineralocorticoid receptor antagonist, a phosphodiesterase inhibitor, an antidiabetic agent, a protease inhibitor, an elastase inhibitor, an anti-inflammatory agent, an antioxidant, an angiogenesis-modulating agent, an agent for treating osteoporosis, hormone replacement therapy, a hormone receptor-modulating agent, an oral contraceptive, an anti-obesity drug, an antidepressant drug, an antianxiety agent, an antipsychotic agent, an antiproliferative agent, an antitumor agent, antiulcer and anti-gastroesophageal reflux agents, a growth hormone agent and/or a growth hormone secretagogue, a thyroid-mimetic, an anti-infective agent, an antiviral agent, an antimicrobial agent, an antifungal agent, a drug for treating hypercholesterolemia/dyslipidemia and therapy for improving lipid profile, preconditioning of simulated ischemia and/or an agent for stunned myocardium, a combination thereof and the like.

In another embodiment, examples of the combined agent in the present invention further include an antiarrhythmic agent, an antihypertensive agent, an anticoagulant agent, an antiplatelet agent, a thrombolytic agent, a fibrinolytic agent, a calcium channel blocker, a potassium channel blocker, a cholesterol/lipid-lowering agent, a serine protease inhibitor, an elastase inhibitor, an anti-inflammatory agent, a combination thereof and the like.

Examples of the antiarrhythmic agent include an IKur inhibitor, an elastase inhibitor, a serine protease inhibitor, a steroid and the like.

Examples of the antihypertensive agent include an ACE inhibitor, an AT-1 receptor antagonist, a β-adrenergic receptor antagonist, an ETA receptor antagonist, a dual ETA/AT-1 receptor antagonist, a vasopeptidase inhibitor and the like.

In a preferable embodiment, examples of the combined agent in the present invention include an antiplatelet agent and a combination thereof.

The combined medicine of the compound of the present invention with the above-described other agent(s) may be administered in the form of a compounding agent in which both ingredients are compounded in a preparation or may be administered in the form of separate preparations by the same route of administration or different routes of administration. When the separate preparations are administered, the preparations are not necessarily administered concomitantly, but as needed, each of the preparations may be administered with a time difference. In addition, in the case of the administrations with a time difference, the order of administrations is not particularly limited, but may be appropriately adjusted in order to achieve the desired drug efficacy.

The dose of the above-described other agent(s) which is used in combination with the compound of the present invention can be appropriately increased or decreased based on the clinically used dose of the agent(s) or an agent similar thereto. In addition, the compounded ratio of the compound of the present invention and other agent(s) can be appropriately adjusted by considering the age and body weight of the subject of administration, the method for administration, the duration of administration, the target disease, the symptom and the like. Approximately 0.01 to 100 parts by weight of other agent(s) may be combined with 1 part by weight of the compound of the present invention. Two or more kinds of other agent(s) may be used. In addition, examples of the other agent(s) include not only those listed above, but also drug(s) having the same mechanism as those listed above. The drug(s) having the same mechanism as those listed above includes not only those which have been found up to now but also those which will be found in future.

The compound of the present invention is normally administered systemically or locally, in the form of an oral preparation or a parenteral preparation. Examples of the oral preparation include an oral liquid preparation (such as an elixir, a syrup, a pharmaceutically acceptable liquid agent, a suspension and an emulsion), an oral solid preparation (such as a tablet (including a sublingual tablet and an orally disintegrating tablet), a pill, a capsule (including a hard capsule, a soft capsule, a gelatin capsule and a microcapsule), a powdered agent, a granule and a lozenge) and the like. Examples of the parenteral preparation include a liquid preparation (such as an injection preparation (such as an intravitreal injection preparation, a subcutaneous injection preparation, an intravenous injection preparation, an intramuscular injection preparation, an intraperitoneal injection preparation and a preparation for drip infusion), an eye drop (such as an aqueous eye drop (such as an aqueous ophthalmic solution, an aqueous ophthalmic suspension, a viscous eye drop and a solubilized eye drop) and a non-aqueous eye drop (such as a non-aqueous ophthalmic solution and a non-aqueous ophthalmic suspension))), an external preparation (such as an ointment (such as an ophthalmic ointment)), an ear drop and the like. The above-described preparation may be a controlled-release preparation such as an immediate-release preparation and a sustained release preparation. The above-described preparation can be prepared by a known method, for example, by a method described in Pharmacopeia of Japan or the like.

The oral liquid preparation as an oral preparation is prepared, for example, by dissolving, suspending or emulsifying an active ingredient in a generally used diluent (such as purified water, ethanol and a mixed liquid thereof). In addition, the liquid preparation may further contain a wetting agent, a suspending agent, an emulsifying agent, a sweetening agent, a flavoring agent, a perfume, a preservative, a buffer agent and the like.

The oral solid preparation as an oral preparation is prepared, for example, by mixing an active ingredient with an excipient (such as lactose, mannitol, glucose, microcrystalline cellulose and starch), a bonding agent (such as hydroxypropyl cellulose, polyvinylpyrrolidone and magnesium aluminometasilicate), a disintegrating agent (such as calcium cellulose glycolate), a lubricant (such as magnesium stearate), a stabilizer, a solubilizing agent (such as glutamic acid and aspartic acid) and the like by a routine procedure. In addition, if necessary, the active ingredient may be coated with a coating agent (such as white soft sugar, gelatin, hydroxypropyl cellulose and hydroxypropyl methylcellulose phthalate) or may be coated with two or more layers.

The external preparation as a parenteral preparation is prepared by a known method or according to a normally used formulation. For example, an ointment is prepared by triturating or melting an active ingredient in a base. An ointment base is selected from those which are known and those which are normally used. For example, one selected from the followings is used or two or more kinds selected from the followings are used by being mixed together: a higher fatty acid or a higher fatty acid ester (such as adipic acid, myristic acid, palmitic acid, stearic acid, oleic acid, an adipate, a myristate, a palmitate, a stearate and an oleate), waxes (such as beeswax, whale wax and ceresin), a surface-active agent (such as a polyoxyethylene alkyl ether phosphoric ester), a higher alcohol (such as cetanol, stearyl alcohol and cetostearyl alcohol), a silicone oil (such as dimethyl polysiloxane), hydrocarbons (such as hydrophilic petrolatum, white petrolatum, purified lanolin and liquid paraffin), glycols (such as ethylene glycol, diethylene glycol, propylene glycol, polyethylene glycol and macrogol), a vegetable oil (such as castor oil, olive oil, sesame oil and turpentine oil), an animal oil (such as mink oil, egg-yolk oil, squalane and squalene), water, an absorption promoter and an agent for preventing skin rash. In addition, a moisturizing agent, a preservative, a stabilizing agent, an antioxidant, a flavoring agent and the like may be contained.

The injection preparation as a parenteral preparation includes a solution, a suspension, an emulsion and a solid injection preparation which is used at the time of use by being dissolved or suspended in a solvent. The injection preparation is used, for example, by dissolving, suspending or emulsifying an active ingredient in a solvent. Examples of the solvent used include distilled water for injection, saline, a vegetable oil, alcohols such as propylene glycol, polyethylene glycol and ethanol and the like as well as a mixture thereof. In addition, the injection preparation may contain a stabilizer, a solubilizing agent (such as glutamic acid, aspartic acid and polysorbate 80 (registered trademark)), a suspending agent, an emulsifying agent, an analgesic, a buffer agent, a preservative and the like. The above-described injection preparation is prepared by being sterilized at the final process or by an aseptic manipulation method. In addition, the above-described injection preparation can be also used by preparing a sterile solid preparation, for example, a lyophilized preparation, and dissolving the sterile solid preparation in sterilized or sterile distilled water for injection or other solvent before use of the preparation.

In order to use the compound of the present invention or the combined medicine of the compound of the present invention with other agent(s) for the above-described purpose, the compound of the present invention or the combined medicine of the compound of the present invention with other agent(s) is normally administered systemically or locally, in the form of an oral preparation or a parenteral preparation. The dose varies depending on the age, the body weight, the symptom, the therapeutic effect, the method for administration, the duration of the treatment and the like. However, normally, the dose per adult is in the range of from 1 ng to 1,000 mg per administration, from one to several oral administrations per day or the dose per adult is in the rage of from 0.1 ng to 10 mg per administration, from one to several parenteral administrations per day. Alternatively, the dose is continuously administered intravenously for a period of time in the range of 1 to 24 hours per day. Of course, the dose varies depending on various factors as described above, and therefore, there are some cases in which a dose below the above-described dose is sufficient and there are other cases in which administration of a dose which exceeds the above-described range is required.

EXAMPLES

The present invention will be described in details by referring to Examples hereinbelow, but the present invention is not limited to Examples.

Concerning chromatographic separation or TLC, a solvent in parentheses corresponds to an eluting solvent or a developing solvent employed and a ratio is expressed by volume ratio.

Concerning NMR, a solvent in parentheses corresponds to a solvent used for the measurement.

A compound name used in the present specification is given by using a computer program ACD/Name (registered trademark) of Advanced Chemistry Development which generally denominates a compound according to the IUPAC nomenclature or by denomination according to the IUPAC nomenclature.

The measuring time, solvents and column conditions used for LC/MS analyses in the following Examples are shown hereinbelow. Meanwhile, $t_R$ means Retention time.

Condition a. column YMC-Triart C18, 2.0 mm×30 mm, 1.9 m; column temperature 30° C.; mobile phase (Liquid A) 0.1% trifluoroacetic acid aqueous solution and (Liquid B) 0.1% trifluoroacetic acid-acetonitrile solution; flow rate 1.0 mL/min; analysis time 1.5 minutes; gradient: 0 minute (Liquid A/Liquid B=95/5), 0.1 minutes (Liquid A/Liquid B=95/5), 1.2 minutes (Liquid A/Liquid B=5/95), 1.4 minutes (Liquid A/Liquid B=5/95), 1.41 minutes (Liquid A/Liquid B=95/5), 1.5 minutes (Liquid A/Liquid B=95/5)

Condition b. column Waters ACQUITY UPLC (registered trademark) BEH C18, 2.1 mm×30 mm, 1.7 μm; column temperature 40° C.; mobile phase (Liquid A) 0.1% formic acid aqueous solution and (Liquid B) 0.1% formic acid-acetonitrile solution; flow rate 1.0 mL/min; analysis time 1.5 minutes; gradient: 0 minute (Liquid A/Liquid B=95/5), 0.1 minutes (Liquid A/Liquid B=95/5), 1.2 minutes (Liquid A/Liquid B=5/95), 1.4 minutes (Liquid A/Liquid B=5/95), 1.41 minutes (Liquid A/Liquid B=95/5), 1.5 minutes (Liquid A/Liquid B=95/5).

Experimental Examples

Example 1 (1): 2-methyl-2-propanyl (6-fluoro-5-iodo-2-pyridinyl)carbamate

To a solution of 6-fluoro-5-iodopyridin-2-amine (17 g) in acetonitrile (150 mL), di-tert-butyl dicarbonate (17.14 g) and 4-dimethylaminopyridine (0.87 g) were added, and the mixture was stirred at room temperature for 2 hours. Further, to the mixture, di-tert-butyl dicarbonate (7.8 g) was added, and the mixture was stirred at room temperature for additional 2 hours. To the reaction mixture, saturated ammonium chloride aqueous solution and ethyl acetate were added, and insoluble matters were removed. The combined organic layers were washed with saturated saline, were dried, and thereafter, were concentrated. The residue was purified by two kinds of column chromatography (ethyl acetate:hexane=0:100 to 25:75), (aminosilica, ethyl acetate:hexane=10:90 to 50:50) to give the title compound (9.2 g) having the following physical property.

TLC: Rf 0.69 (ethyl acetate:hexane=25:75).

Example 1 (2): 2-Methyl-2-Propanyl [5-(1-Ethoxyvinyl)-6-Fluoro-2-Pyridinyl]Carbamate To a solution (200 mL) of the compound (40 g) prepared in Example 1 (1) in N,N-dimethylformamide, tributyl(1-ethoxyethenyl)tin (50 g) was added. The mixture was deaerated with argon, and to the mixture, tetrakis(triphenylphosphine)palladium (0) (3.24 g) was added, and the mixture was stirred at 100° C. for 16 hours. The reaction mixture was diluted with ethyl acetate (200 mL), and was poured into 1 M potassium fluoride aqueous solution (500 mL). The mixture was stirred for 30 minutes, and thereafter, was filtrated through Celite (registered trademark), and the filtrate was extracted with ethyl acetate. The combined organic layers were washed with water and saturated saline, were dried, and thereafter, were concentrated. The residue was purified by column chromatography (aminosilica, ethyl acetate:hexane=3:97 to 5:95) to give the title compound (34.4 g) having the following physical properties.

LC/MS $t_R$ 1.15 minutes: MS (ES$^+$) m/z 227 [M-CH$_2$C(CH$_3$)$_2$)+H](Condition a).

Example 1 (3): 2-Methyl-2-Propanyl [5-(Bromoacetyl)-6-Fluoro-2-Pyridinyl]Carbamate The compound (34.4 g) prepared in Example 1 (2) was dissolved in tetrahydrofuran (150 mL) and water (50 mL), and to the mixture, N-bromosuccinimide (21.7 g) was added under ice cooling. The mixture was stirred for 30 minutes under ice cooling, and thereafter, was diluted with ethyl acetate, and was washed twice with saturated sodium bicarbonate aqueous solution. The organic layer was washed with saturated saline, was dried, and thereafter, was concentrated. The residue was purified by column chromatography (ethyl acetate:hexane=10:90 to 30:70) to give the title compound (27.58 g) having the following physical property.

TLC: Rf 0.26 (ethyl acetate:hexane=10:90).

Example 1 (4): 2-methyl-2-propanyl [5-(2-((3S)-7-[5-chloro-2-(1H-tetrazol-1-yl)phenyl]-5-oxo-1,2,3,5-tetrahydro-3-indolizinyl)-1H-imidazol-5-yl)-6-fluoro-2-pyridinyl]carbamate To a solution (200 mL) of (3S)-7-[5-chloro-2-(1H-1,2,3,4-tetrazol-1-yl)phenyl]-5-oxo-1,2,3,5-tetrahydroindolizine-3-carboxylic acid (described in Example 9 of Patent Literature 6) (27.58 g) and the compound (25.68 g) prepared in Example 1 (3) in N-methylpyrrolidone, N,N-diisopropylethylamine (26.7 mL) was added under ice cooling. The mixture was stirred at room temperature for 30 minutes, and thereafter, the reaction mixture was diluted with ethyl acetate (200 mL) and was washed with saturated ammonium chloride aqueous solution (500 mL). The aqueous layer was extracted with ethyl acetate, and the combined organic layers were washed with water (500 mL) and saturated saline (500 mL), were dried, and thereafter, were concentrated. The residue was dissolved in toluene (500 mL) and glacial acetic acid (50 mL), and to the mixture, ammonium acetate (59.4 g) was added, and the mixture was stirred at 100° C. for 3 hours. The mixture was concentrated under reduced pressure, was diluted with ethyl acetate, and was washed with saturated potassium carbonate aqueous solution (500 mL). The aqueous layer was extracted with ethyl acetate, and the combined organic layers were dried, and thereafter, were concentrated. The residue was purified by column chromatography (ethyl acetate:hexane=50:50 to 100:0) to give the title compound (33.5 g) having the following physical properties.

LC/MS $t_R$ 0.84 minutes: MS (ES$^+$) m/z 590 (M+H) (Condition a).

Example 1 (5): 2-methyl-2-propanyl [5-(2-{(3S)-7-[5-chloro-2-(1H-tetrazol-1-yl)phenyl]-5-oxo-1,2,3,5-tetrahydro-3-indolizinyl}-4-fluoro-1H-imidazol-5-yl)-6-fluoro-2-pyridinyl]carbamate The compound (350 mg) prepared in Example 1 (4) was dissolved in tetrahydrofuran (1.2 mL) and acetonitrile (3.6 mL), and to the mixture, pyridine (0.14 mL) was added, and to the mixture, 1-chloromethyl-4-fluoro-1,4-diazoniabicyclo [2.2.2]octane bis(tetrafluoroborate) (315 mg) was added at −18° C., and the mixture was stirred for 2 hours. The reaction mixture was diluted with ethyl acetate, and sodium sulfite aqueous solution was added, and the mixture was stirred. Water was added to the mixture, and the mixture was subjected to liquid separation, and the aqueous layer was extracted with ethyl acetate. The organic layers were combined, and the combined organic layers were washed with hydrochloric acid, saturated sodium bicarbonate aqueous solution and saturated saline, were dried, and thereafter, were concentrated. The residue was purified by column chromatography (ethyl acetate:hexane=30:70 to 100:0) to give the title compound (138 mg) having the following physical property.

TLC: Rf 0.51 (ethyl acetate:hexane=80:20).

Example 1 (6): (3S)-3-[5-(6-Amino-2-Fluoro-3-Pyridinyl)-4-Fluoro-1H-Imidazol-2-Yl]-7-[5-Chloro-2-(1H-Tetrazol-1-Yl)Phenyl]-2,3-Dihydro-5(1H)-Indolizinone

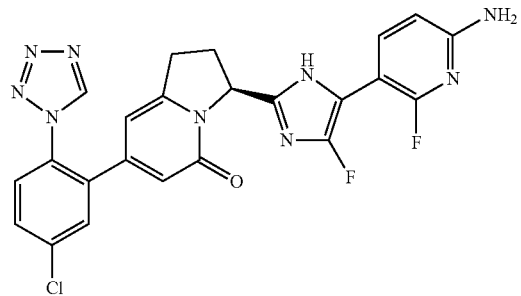 [SMILES: Nc1ccc(-c2[nH]c([C@@H]3CCc4cc(-c5cc(Cl)ccc5-n5cnnn5)cc(=O)n43)nc2F)c(F)n1]

To a solution (100 mL) of the compound (12.2 g) prepared in Example 1 (5) in 1,4-dioxane, concentrated hydrochloric acid (5 mL) was added, and the mixture was stirred at 40° C. for 1 hour. Additional concentrated hydrochloric acid (5 mL) was added, and the mixture was stirred for 1 hour and 30 minutes, and thereafter, the mixture was concentrated. The residue was diluted with ethyl acetate, and was washed with saturated sodium carbonate aqueous solution. The aqueous layer was extracted with 17% methanol/ethyl acetate, and the combined organic layers were dried, and thereafter, were concentrated. The residue was purified by column chromatography (methanol:ethyl acetate=5:95 to 10:90) to give the title compound (8.27 g) having the following physical properties.

TLC: Rf 0.48 (ethyl acetate);
$^1$H-NMR (CD$_3$OD): δ 9.34 (s, 1H), 7.76-7.62 (m, 4H), 6.45 (dd, 1H), 6.13 (s, 1H), 6.07 (s, 1H), 5.71 (d, 1H), 3.42 (m, 1H), 3.06 (m, 1H), 2.58 (m, 1H), 2.42 (m, 1H).

Example 2 (1): 6-Fluoro-5-Iodo-2-Pyridinamine

N-iodosuccinimide (56.5 g) was added in multiple portions (3 portions) to a solution of 6-fluoro-2-pyridinamine (25.6 g) in N,N-dimethylformamide (200 mL) under ice cooling. The mixture was stirred at room temperature for 3 hours, and thereafter, to the reaction liquid, city water (0.5 L) was added. The mixture was extracted three times with ethyl acetate/hexane (1/1, 300 mL), and the organic layer was washed with saturated sulfurous acid aqueous solution (0.5 L), saturated sodium carbonate aqueous solution (0.5 L, twice), city water (0.5 L) and saturated saline (0.5 L), was dried, and thereafter, was concentrated. To the obtained residue, hexane/ethyl acetate (3/1, 150 mL) was added, and the slurry was washed at room temperature, and was filtrated. The obtained solid was dried to give the title compound (36.7 g) having the following physical property.

TLC: Rf 0.56 (ethyl acetate:hexane=1:2).

Example 2 (2): Bis(2-Methyl-2-Propanyl) (6-Fluoro-5-Iodo-2-Pyridinyl)Imidodicarbonate To a solution of the compound (36.7 g) prepared in Example 2 (1) and 4-dimethylaminopyridine (0.9 g) in acetonitrile (300 mL), a solution of di-tert-butyl dicarbonate (74.0 g) in acetonitrile (100 mL) was added, and the mixture was stirred at room temperature for 3 hours. The reaction solution was concentrated, and the obtained residue was dissolved in ethyl acetate (500 mL), and the mixture was washed with saturated ammonium chloride aqueous solution (400 mL), and the aqueous layer was extracted with ethyl acetate (200 mL). The combined organic layers were dried, and thereafter, were concentrated. The obtained residue was purified by silica gel column chromatography (ethyl acetate:hexane=5:95 to 10:90) to give the title compound (45.06 g) having the following physical properties.
$^1$H-NMR (CDCl$_3$): δ 8.14 (t, 1H), 7.03 (dd, 1H), 1.47 (s, 18H).

Example 2 (3): 2-Methyl-2-Propanyl (5-Cyano-6-Fluoro-2-Pyridinyl)Carbamate

A solution of the compound (9.1 g) prepared in Example 2 (2), zinc (II) cyanide (7.32 g) and tetrakis(triphenylphosphine)palladium (0) (1.2 g) in 1-methyl-2-pyrrolidinone (60 mL) was deaerated under reduced pressure. Under microwave irradiation, the mixture was stirred at 130° C. for 1 hour, and thereafter, was left to cool. The reaction solution was diluted with ethyl acetate (100 mL), and thereafter, was filtrated through Celite to remove insoluble matters, and the insoluble matters were washed with ethyl acetate (50 mL). The filtrate was subjected to liquid separation, and the aqueous layer was extracted again with ethyl acetate (100 mL). The organic layers were combined, were dried, and thereafter, were concentrated. The obtained residue was purified by silica gel column chromatography (ethyl acetate:hexane=5:95 to 80:20) to give the title compound (2.1 g) having the following physical property.

TLC: Rf 0.25 (ethyl acetate:hexane=10:90).

Example 2 (4): 2-Methyl-2-Propanyl [6-Fluoro-5-(N-Hydroxycarbamimidoyl)-2-Pyridinyl]Carbamate To a solution of the compound (1.56 g) prepared in Example 2 (3) and hydroxylamine hydrochloride (0.91 g) in ethanol (40 mL), N,N-diisopropylethylamine (2.84 mL) was added, and the mixture was stirred at 40° C. overnight. The reaction solution was concentrated, and the obtained residue was dissolved in ethyl acetate (50 mL). To the mixture, city water (50 mL) was added to wash, and thereafter, the organic layer was dried, and thereafter, was concentrated to give the crude title compound (1.93 g) having the following physical properties.

LC/MS t$_R$ 0.60 minutes; MS (ES+) m/z 271 (M+H) (Condition a).

Example 2 (5): 2-Methyl-2-Propanyl (5-Carbamimidoyl-6-Fluoro-2-Pyridinyl)Carbamate Acetate To a solution of the compound (1.93 g) prepared in Example 2 (4) in acetic acid (10 mL), acetic anhydride (0.75 mL) was added, and the mixture was stirred at room temperature for 1 hour. To the reaction liquid, palladium (II) hydroxide (20%, 250 mg) was added, and the mixture was stirred under hydrogen atmosphere at room temperature for 3 hours. The reaction liquid was filtrated through Celite, and the filtrate was concentrated under reduced pressure to give the crude title compound (2.99 g) having the following physical properties.

LC/MS t$_R$ 0.59 minutes; MS (ES+) m/z 255 (M+H) (Condition a).

Example 2 (6): 2-Methyl-2-Propanyl (5-Carbamimidoyl-6-Fluoro-2-Pyridinyl)Carbamate Hydrochloride To a solution of the compound (2.6 g) prepared in Example 2 (5) in methanol (10 mL), 10% hydrogen chloride/methanol (6.5 mL) solution was added, and the mixture was stirred at room temperature for 10 minutes. To the reaction liquid, toluene was added, and the mixture was concentrated to give the crude title compound (2.63 g) having the following physical properties.

LC/MS t$_R$ 0.58 minutes; MS (ES+) m/z 255 (M+H) (Condition a).

Example 2 (7): (3S)-3-(Chloroacetyl)-7-[5-Chloro-2-(1H-Tetrazol-1-Yl)Phenyl]-2,3-Dihydro-5(1H)-Indolizinone To a solution of (3S)-7-[5-chloro-2-(1H-1,2,3,4-tetrazol-1-yl)phenyl]-5-oxo-1,2,3,5-tetrahydroindolizine-3-carboxylic acid (described in Example 9 of Patent Literature 6) (3.0 g) in dichloromethane (15 mL), 1-chloro-N,N,2-trimethyl-1-propen-1-amine (1.33 mL) was added under ice cooling, and the mixture was stirred at 0° C. for 40 minutes. To the mixture, trimethylsilyldiazomethane (2 M hexane solution, 8.4 mL) was added, and thereafter, the mixture was stirred at 0° C. for additional 1 hour. To the mixture, concentrated hydrochloric acid (0.87 mL) was added under ice cooling, and the mixture was stirred at room temperature for 20 minutes. To the reaction liquid, city water (50 mL) was added, and the mixture was extracted twice with dichloromethane (50 mL). The organic layer was dried, and thereafter, was concentrated, and the obtained residue was purified by silica gel column chromatography (ethyl acetate: hexane=40:60 to 100:0) to give the title compound (2.32 g) having the following physical properties.

LC/MS $t_R$ 0.80 minutes; MS (ES+) m/z 390 (M+H) (Condition a).

Example 2 (8): 2-methyl-2-propanyl [5-(5-{7-[5-chloro-2-(1H-tetrazol-1-yl)phenyl]-5-oxo-1,2,3,5-tetrahydro-3-indolizinyl}-1H-imidazol-2-yl)-6-fluoro-2-pyridinyl]carbamate To a solution of the compound (1.5 g) prepared in Example 2 (6) and the compound (1.0 g) prepared in Example 2 (7) in acetonitrile (50 mL), potassium carbonate (0.70 g) was added, and the mixture was stirred at 80° C. for 17 hours. The reaction solution was diluted with ethyl acetate (100 mL), and thereafter, the solution was washed with city water (100 mL) and saturated saline (200 mL), was dried, and thereafter, was concentrated. The obtained residue was purified by silica gel column chromatography (ethyl acetate:hexane=50:50 to 100:0, followed by methanol:ethyl acetate=5:95) to give the title compound (1.11 g) having the following physical properties.

LC/MS $t_R$ 0.81 minutes; MS (ES+) m/z 590 (M+H) (Condition a).

Example 2 (9): 2-methyl-2-propanyl [5-(5-{(3S)-7-[5-chloro-2-(1H-tetrazol-1-yl)phenyl]-5-oxo-1,2,3,5-tetrahydro-3-indolizinyl}-4-fluoro-1H-imidazol-2-yl)-6-fluoro-2-pyridinyl]carbamate and 2-methyl-2-propanyl [5-(5-{(3R)-7-[5-chloro-2-(1H-tetrazol-1-yl)phenyl]-5-oxo-1,2,3,5-tetrahydro-3-indolizinyl}-4-fluoro-1H-imidazol-2-yl)-6-fluoro-2-pyridinyl] carbamate To a suspension of the compound (264 mg) prepared in Example 2 (8) and sodium carbonate (118 mg) in acetonitrile (10 mL)/tetrahydrofuran (5 mL), 1-chloromethyl-4-fluoro-1,4-diazoniabicyclo[2.2.2]octane bis(tetrafluoroborate) (selectfluor (registered trademark)) (95 mg) was added, and the mixture was stirred under cooling in an ice/brine bath for 3 hour. The reaction solution was diluted with ethyl acetate (20 mL), and to the solution, sodium sulfite aqueous solution (40 mL) was added. The aqueous layer was extracted twice with ethyl acetate (50 mL), and the combined organic layers were dried, and thereafter, were concentrated. The obtained residue was purified by silica gel column chromatography (aminosilica, ethyl acetate:hexane=50:50 to 100:0, followed by methanol:ethyl acetate=5:95) to give the mixture (71.2 mg) of the S-configuration compound and the R-configuration compound of Example 2 (9). The obtained mixture (20 mg) was purified by the optical resolution (DAICEL, CHIRALFLASH (registered trademark) IC column, (particle size: 20 μm; column length: 100×30 mm I.D.), flow rate: 24 mL/min; column temperature: room temperature; mobile phase (A): acetonitrile; mobile phase (B): methanol; isocratic (mobile phase (A): mobile phase (B)=90:10), 20 minutes; detector: UV Yamazen UV-254W UV-Detector) to give the title compounds (the S-configuration compound of Example 2 (9): 7.9 mg, and the R-configuration compound of Example 2 (9): 7.7 mg). Meanwhile, when the optical resolution was conducted under the above-described conditions, the retention times of the title compounds were 13 minutes (the S-configuration compound of Example 2 (9)) and 9.5 minutes (the R-configuration compound of Example 2 (9)), respectively.

The physical properties of each of the title compounds when being analyzed under liquid chromatographic conditions in parentheses below are shown hereinbelow.

The S-configuration compound of Example 2 (9):

LC $t_R$ 10.4 minutes (column: DAICEL CHIRALPAK (registered trademark) IC 5 μm 4.6 mm×250 mm, mobile phase:acetonitrile/methanol=90/10, flow rate: 1.0 mL/min).

The R-configuration compound of Example 2 (9):

LC $t_R$ 7.95 minutes (column: DAICEL CHIRALPAK (registered trademark) IC 5 μm 4.6 mm×250 mm, mobile phase:acetonitrile/methanol=90/10, flow rate: 1.0 mL/min).

Example 2 (10): (3S)-3-[2-(6-Amino-2-Fluoro-3-Pyridinyl)-4-Fluoro-1H-Imidazol-5-Yl]-7-[5-Chloro-2-(1H-Tetrazol-1-Yl)Phenyl]-2,3-Dihydro-5(1H)-Indolizinone

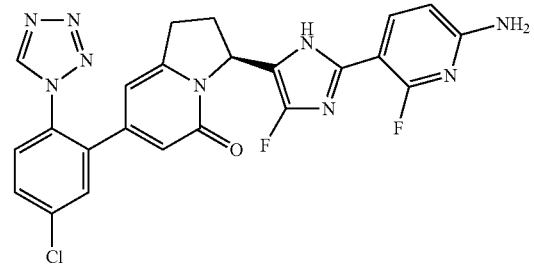 [SMILES: Nc1ccc(-c2nc(F)c([C@@H]3CCc4cc(-c5cc(Cl)ccc5-n5cnnn5)cc(=O)n43)[nH]2)c(F)n1]

To a suspension of the S-configuration compound (436 mg) of Example 2 (9) in ethyl acetate (6 mL), concentrated hydrochloric acid (2 mL) was added, and the mixture was stirred at room temperature for 20 minutes. The reaction solution was concentrated under reduced pressure, and the obtained residue was redissolved in tetrahydrofuran (10 mL). To the solution, saturated sodium bicarbonate aqueous solution (20 mL) was added, and the mixture was extracted with ethyl acetate (20 mL, twice). The organic layers were combined, were dried, and thereafter, were concentrated. The obtained residue was purified by silica gel column chromatography (aminosilica, methanol:ethyl acetate=0:100 to 5:95) to give the title compound (321 mg) having the following physical properties. In addition, the absolute configuration of this compound was determined by X-ray crystallography which used a single crystal of the complex of the compound of the present invention and FXIa.

TLC: Rf 0.60 (methanol:ethyl acetate=5:95);

$^1$H-NMR (CD$_3$OD): δ 9.31 (s, 1H), 7.91 (dd, 1H), 7.74-7.65 (m, 3H), 6.44 (dd, 1H), 6.21 (s, 1H), 6.03 (s, 1H), 5.83 (dd, 1H), 3.39-3.06 (m, 2H), 2.62-2.48 (m, 2H);

LC $t_R$ 22.5 minutes (column DAICEL CHIRALPAK (registered trademark) IC 5 μm 4.6 mm×250 mm, mobile phase: hexane/ethyl acetate=30/70, flow rate: 1.0 mL/min); $[α]^{25}_D$=+44.1° (CH$_3$OH, c=1.00).

Example 2 (11): (3S)-3-[2-(6-Amino-2-Fluoro-3-Pyridinyl)-4-Fluoro-1H-Imidazol-5-Yl]-7-[5-Chloro-2-(1H-Tetrazol-1-Yl)Phenyl]-2,3-Dihydro-5(1H)-Indolizinone Dihydrochloride

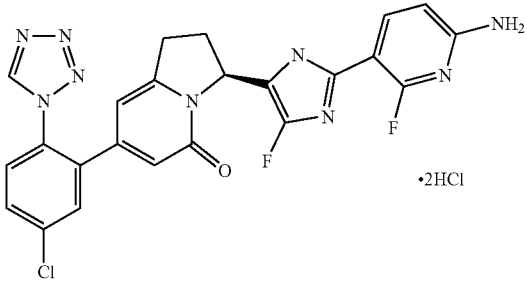 [SMILES: Nc1ccc(-c2nc(F)c([C@@H]3CCc4cc(-c5cc(Cl)ccc5-n5cnnn5)cc(=O)n43)[nH]2)c(F)n1]

To a solution of the S-configuration compound (43 mg) of Example 2 (9) in dichloromethane (4 mL), trifluoroacetic acid (1 mL) was added, and the mixture was stirred at room temperature for 70 minutes. The reaction solution was concentrated under reduced pressure, and the residue was subjected to fractionated purification by high performance liquid chromatography (mobile phase B (0.1% trifluoroacetic acid/acetonitrile):mobile phase A (0.1% trifluoroacetic acid aqueous solution)=5:95 to 95:5). The obtained product was redissolved in ethyl acetate, and to the mixture, an excess amount of 4 M hydrochloric acid/ethyl acetate solution was added, and the mixture was concentrated and was dried to give the title compound (28 mg) having the following physical properties.

LC/MS $t_R$ 0.83 minutes; MS (ES+) m/z 508 (M+H) (Condition a);

$^1$H-NMR (d$_6$-DMSO): δ 11.7 (brs, 1H), 9.64 (s, 1H), 7.87 (dd, 1H), 7.79 (brs, 2H), 7.75 (brs, 1H), 6.38 (dd, 1H), 6.00 (s, 1H), 5.92 (s, 1H), 5.69 (d, 1H), 3.23-2.96 (m, 2H), 2.58-2.22 (m, 2H).

Example 2 (12): (3R)-3-[2-(6-Amino-2-Fluoro-3-Pyridinyl)-4-Fluoro-1H-Imidazol-5-Yl]-7-[5-Chloro-2-(1H-Tetrazol-1-Yl)Phenyl]-2,3-Dihydro-5(1H)-Indolizinone

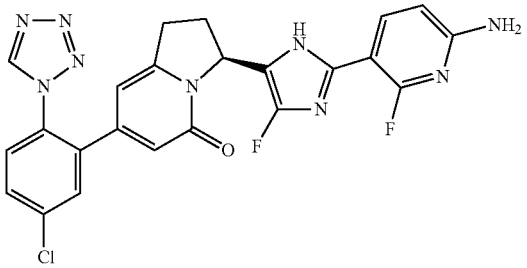 [SMILES: Nc1ccc(-c2nc(F)c([C@@H]3CCc4cc(-c5cc(Cl)ccc5-n5cnnn5)cc(=O)n43)[nH]2)c(F)n1]

The same procedure as in Example 2 (10) was carried out by using the R-configuration compound of Example 2 (9) to give the title compound having the following physical properties.

$^1$H-NMR (CD$_3$OD): δ 9.31 (s, 1H), 7.91 (dd, 1H), 7.74-7.65 (m, 3H), 6.44 (dd, 1H), 6.21 (s, 1H), 6.03 (s, 1H), 5.83 (dd, 1H), 3.39-3.06 (m, 2H), 2.62-2.48 (m, 2H);

LC $t_R$ 13.6 minutes (column DAICEL CHIRALPAK (registered trademark) IC 5 m 4.6 mm×250 mm, mobile phase: hexane/ethyl acetate=30/70, flow rate: 1.0 mL/min); $[α]^{23}_D$=−39.6° (CH$_3$OH, c=1.00).

Example 2 (13): (3S)-3-[2-(6-Amino-2-Fluoro-3-Pyridinyl)-4-Fluoro-1H-Imidazol-5-Yl]-7-[5-Chloro-2-(1H-Tetrazol-1-Yl)Phenyl]-2,3-Dihydro-5(1H)-Indolizinone Dihydrate

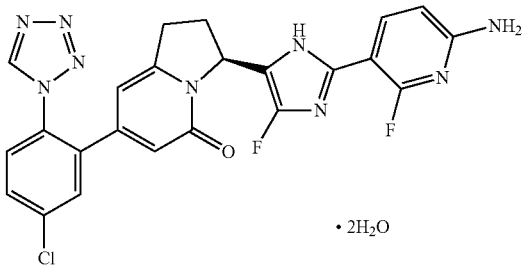 [SMILES: Nc1ccc(-c2nc(F)c([C@@H]3CCc4cc(-c5cc(Cl)ccc5-n5cnnn5)cc(=O)n43)[nH]2)c(F)n1]

The compound (100 mg) of Example 2 (10) was dissolved in acetonitrile (1.0 mL) and water (0.018 mL) by heating at 75° C., and thereafter, the mixture was stirred at 40° C. for 2 hours, and was stirred at room temperature for 30 minutes, and the produced precipitate was obtained by filtration, and was dried under reduced pressure to give the title compound (76 mg).

$^1$H-NMR (CD$_3$OD): δ 9.31 (s, 1H), 7.91 (dd, 1H), 7.74-7.65 (m, 3H), 6.44 (dd, 1H), 6.21 (s, 1H), 6.03 (s, 1H), 5.83 (dd, 1H), 3.39-3.06 (m, 2H), 2.62-2.48 (m, 2H);

LC/MS $t_R$ 0.82 minutes; MS (ES+) m/z 508 (M+H) (Condition a).

Comparative Example 2 (1): (3S)-3-[2-(6-amino-2-fluoro-3-pyridinyl)-1H-imidazol-5-yl]-7-[5-chloro-2-(1H-tetrazol-1-yl)phenyl]-2,3-dihydro-5(1H)-indolizinone

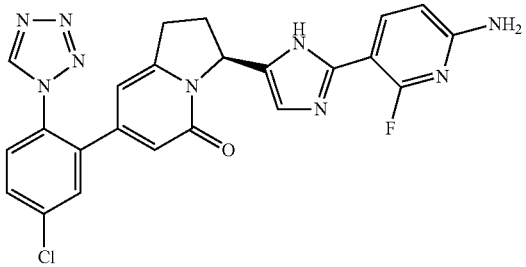 [SMILES: Nc1ccc(-c2ncc([C@@H]3CCc4cc(-c5cc(Cl)ccc5-n5cnnn5)cc(=O)n43)[nH]2)c(F)n1]

The compound prepared in Example 2 (8) was subjected to the optical resolution, and the same procedure as in Example 2 (10) was carried out to give the title compound.

Comparative Example 2 (2): 2-methyl-2-propanyl [5-(4-chloro-5-{7-[5-chloro-2-(1H-tetrazol-1-yl)phenyl]-5-oxo-1,2,3,5-tetrahydro-3-indolizinyl}-1H-imidazol-2-yl)-6-fluoro-2-pyridinyl]carbamate A solution of the compound (1.47 g) prepared in Example 2 (8) in THF (28 mL) was cooled to 0° C., and to the solution, 1,3-dichloro-5,5-dimethylhydantoin (491 mg) was added, and the mixture was stirred for 30 minutes. To the reaction mixture, sodium sulfite aqueous solution was added to degrade the reagent, and to the mixture, water was added, and the mixture was extracted with ethyl acetate. The obtained organic layer was washed with water, 1 M sodium hydroxide aqueous solution and saturated saline, was dried over anhydrous sodium sulfate, and thereafter, was concentrated under reduced pressure. The obtained residue was purified by silica gel column chromatography (ethyl acetate: hexane=70:30 to 100:0) to give the title compound (1.10 g).

Comparative Example 2 (3): (3S)-3-[2-(6-amino-2-fluoro-3-pyridinyl)-4-chloro-1H-imidazol-5-yl]-7-[5-chloro-2-(1H-tetrazol-1-yl)phenyl]-2,3-dihydro-5(1H)-indolizinone

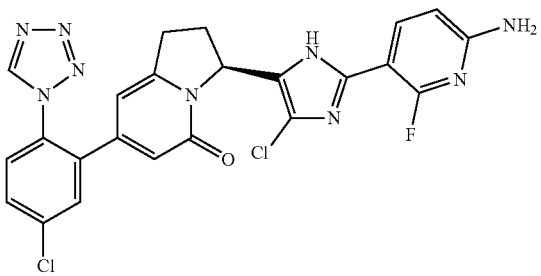 [SMILES: Nc1ccc(-c2nc(Cl)c([C@@H]3CCc4cc(-c5cc(Cl)ccc5-n5cnnn5)cc(=O)n43)[nH]2)c(F)n1]

The compound prepared in Comparative Example 2 (2) was subjected to the optical resolution, and the same procedure as in Example 2 (10) was carried out to give the title compound.

Comparative Example 2 (4): Bis(2-Methyl-2-Propanyl) (5-Carbamimidoyl-2-Pyridinyl)Imidedicarbonate Hydrochloride The same procedure as in Example 2 (2)→Example 2 (4)→Example 2 (5)→Example 2 (6) was carried out by using 6-aminonicotinonitrile instead of the compound prepared in Example 2 (1) to give the title compound.

Comparative Example 2 (5): (3S)-3-[2-(6-Amino-3-Pyridinyl)-4-Fluoro-1H-Imidazol-5-Yl]-7-[5-Chloro-2-(1H-Tetrazol-1-Yl)Phenyl]-2,3-Dihydro-5(1H)-Indolizinone

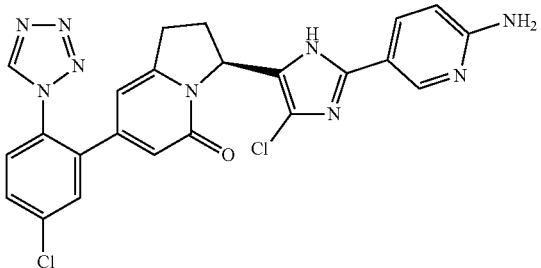 [SMILES: Nc1ccc(-c2nc(Cl)c([C@@H]3CCc4cc(-c5cc(Cl)ccc5-n5cnnn5)cc(=O)n43)[nH]2)cn1]

The same procedure as in Example 2 (8)→Example 2 (9)→Example 2 (10) was carried out by using the compound prepared in Example 2 (7) and the compound prepared in Comparative Example 2 (4) to give the title compound.

Example 3 (1): (6S)-6-(chloroacetyl)-2-[5-chloro-2-(1H-tetrazol-1-yl)phenyl]-7,8-dihydropyrrolo[1,2-a]pyrimidin-4(6H)-one The same procedure as in Example 2 (7) was carried out by using (6S)-2-[5-chloro-2-(1H-1,2,3,4-tetrazol-1-yl)phenyl]-4-oxo-4H,6H,7H,8H-pyrrolo[1,2-a]pyrimidine-6-carboxylic acid (described in Example 336 of Patent Literature 6) to give the title compound having the following physical properties.

LC/MS $t_R$ 0.75 minutes; MS (ES+) m/z 391 (M+H) (Condition a).

Example 3 (2): 2-methyl-2-propanyl [5-(5-(2-[5-chloro-2-(1H-tetrazol-1-yl)phenyl]-4-oxo-4,6,7,8-tetrahydropyrrolo[1,2-a]pyrimidin-6-yl)-1H-imidazol-2-yl)-6-fluoro-2-pyridinyl]carbamate The same procedure as in Example 2 (8) was carried out by using the compound prepared in Example 2 (6) and the compound of Example 3 (1) to give the title compound having the following physical properties.

LC/MS $t_R$ 0.79 minutes; MS (ES+) m/z 591 (M+H) (Condition a).

Example 3 (3): 2-methyl-2-propanyl [5-(5-{(6S)-2-[5-chloro-2-(1H-tetrazol-1-yl)phenyl]-4-oxo-4,6,7,8-tetrahydropyrrolo[1,2-a]pyrimidin-6-yl}-4-fluoro-1H-imidazol-2-yl)-6-fluoro-2-pyridinyl]carbamate and 2-methyl-2-propanyl [5-(5-{(6R)-2-[5-chloro-2-(1H-tetrazol-1-yl)phenyl]-4-oxo-4,6,7,8-tetrahydropyrrolo[1,2-a]pyrimidin-6-yl}-4-fluoro-1H-imidazol-2-yl)-6-fluoro-2-pyridinyl]carbamate The same procedure as in Example 2 (9) was carried out by using the compound prepared in Example 3 (2) to give the title compound having the following physical properties. Meanwhile, when the optical resolution (DAICEL, CHIRALFLASH (registered trademark) IC column, (particle size: 20 μm; column length: 100×30 mm I.D.), flow rate: 24 mL/min; column temperature: room temperature; mobile phase:acetonitrile; detector: UV Yamazen UV-254W UV-Detector) was conducted, the retention times of the title compounds were 13.7 minutes (the S-configuration compound of Example 3 (3)) and 8.1 minutes (the R-configuration compound of Example 3 (3)), respectively.

The physical properties of each of the title compounds when being analyzed under liquid chromatographic conditions in parentheses below are shown hereinbelow.

The S-configuration compound of Example 3 (3):

LC $t_R$ 4.15 minutes (column DAICEL CHIRALPAK (registered trademark) IC 3 μm 4.6 mm×250 mm, mobile phase:methanol, flow rate: 1.0 mL/min).

The R-configuration compound of Example 3 (3):

LC $t_R$ 3.75 minutes (column DAICEL CHIRALPAK (registered trademark) IC 3 μm 4.6 mm×250 mm, mobile phase:methanol, flow rate: 1.0 mL/min).

Example 3 (4): (6S)-6-[2-(6-Amino-2-Fluoro-3-Pyridinyl)-4-Fluoro-1H-Imidazol-5-Yl]-2-[5-Chloro-2-(1H-Tetrazol-1-Yl)Phenyl]-7,8-Dihydropyrrolo[1,2-a]Pyrimidin-4(6H)-One

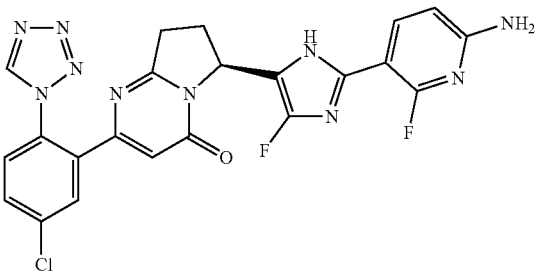 [SMILES: Nc1ccc(-c2nc(F)c([C@@H]3CCc4nc(-c5cc(Cl)ccc5-n5cnnn5)cc(=O)n43)[nH]2)c(F)n1]

The same procedure as in Example 2 (10) was carried out by using the S-configuration compound of Example 3 (3) to give the title compound having the following physical properties.

TLC: Rf 0.65 (methanol:ethyl acetate=5:95);

$^1$H-NMR (CD$_3$OD): δ 9.40 (s, 1H), 7.95-7.86 (m, 2H), 7.76 (dd, 1H), 7.68 (d, 1H), 6.44 (dd, 1H), 6.41 (s, 1H), 5.78 (dd, 1H), 3.12 (m, 1H), 2.90 (m, 1H), 2.62 (m, 1H) 2.41 (m, 1H);

LC t$_R$ 4.23 minutes (column DAICEL CHIRALPAK (registered trademark) IC 3 m 4.6 mm×250 mm, mobile phase: methanol, flow rate: 1.0 mL/min);

[α]$^{25}_D$=+74.6° (CH$_3$OH, c=1.00).

Example 3 (5): (6R)-6-[2-(6-amino-2-fluoro-3-pyridinyl)-4-fluoro-1H-imidazol-5-yl]-2-[5-chloro-2-(1H-tetrazol-1-yl)phenyl]-7,8-dihydropyrrolo[1,2-a]pyrimidin-4(6H)-one dihydrochloride

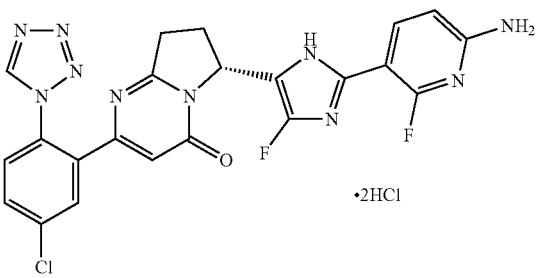 [SMILES: Nc1ccc(-c2nc(F)c([C@H]3CCc4nc(-c5cc(Cl)ccc5-n5cnnn5)cc(=O)n43)[nH]2)c(F)n1]

The same procedure as in Example 2 (11) was carried out by using the R-configuration compound of Example 3 (3) to give the title compound having the following physical properties.

$^1$H-NMR (CD$_3$OD): δ 9.44 (s, 1H), 7.95-7.85 (m, 2H), 7.78 (dd, 1H), 7.71 (d, 1H), 6.50 (dd, 1H), 6.42 (s, 1H), 5.80 (dd, 1H), 3.13 (m, 1H), 2.98 (m, 1H), 2.72 (m, 1H) 2.43 (m, 1H);

LC t$_R$ 4.63 minutes (column DAICEL CHIRALPAK (registered trademark) IC 3 μm 4.6 mm×250 mm, mobile phase:methanol, flow rate: 1.0 mL/min).

Comparative Example 3 (1): methyl[4-(4-chloro-5-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-2-yl)phenyl]carbamate

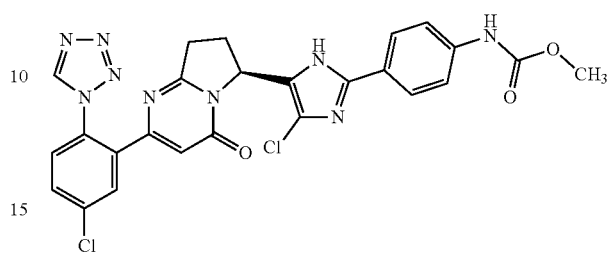

A compound obtained by carrying out the same procedure as in Example 2 (8) to Comparative Example 2 (2) by using the compound synthesized in Example 3 (1) and the compound described in Example 237 of Patent Literature 6 was subjected to the optical resolution to give the title compound.

Example 4 (1): Ethyl (3S)-7-(2-Azido-5-Chlorophenyl)-5-Oxo-1,2,3,5-Tetrahydro-3-Indolizinecarboxylate To a solution (15 mL) of ethyl (3S)-7-(2-amino-5-chlorophenyl)-5-oxo-1,2,3,5-tetrahydroindolizine-3-carboxylate (described in Example 7 of Patent Literature 6) (2.0 g) in acetonitrile, trimethylsilyl azide (1.39 g) and amyl nitrite (1.41 g) were added with cooling (0° C.). The mixture was stirred at room temperature for 1 hour, and thereafter, was concentrated. The residue was purified by column chromatography (ethyl acetate:hexane=10:90 to 100:0) to give the title compound (1.89 g) having the following physical property.

TLC: Rf 0.75 (methanol:ethyl acetate=5:95).

Example 4 (2): Ethyl (3S)-7-[2-(4-Carbamoyl-1H-1,2,3-Triazol-1-Yl)-5-Chlorophenyl]-5-Oxo-1,2,3,5-Tetrahydro-3-Indolizinecarboxylate To a solution (45 mL) of the compound (15.0 g) prepared in Example 4 (1) in N,N-dimethylformamide, propiolamide (3.18 g), (R)-3,4-dihydroxy-5-((S)-1,2-dihydroxyethyl)furan-2(5H)-one (1.47 g) and copper (II) sulfate (0.33 g) were added. The mixture was stirred at 50° C. for 10 minutes, and thereafter, to the mixture, water was added. The precipitate was obtained by filtration, was washed with water, and thereafter, was dried to give the title compound (17.5 g) having the following physical properties.

LC/MS t$_R$ 0.69 minutes: MS (ES$^+$) m/z 428 (M+H) (Condition b).

Example 4 (3): (3S)-7-[2-(4-Carbamoyl-1H-1,2,3-Triazol-1-Yl)-5-Chlorophenyl]-5-Oxo-1,2,3,5-Tetrahydro-3-Indolizinecarboxylic Acid To a solution (10 mL) of the compound (100 mg) prepared in Example 4 (2) in 1,4-dioxane, 5 M hydrochloric acid (5 mL) was added. The mixture was stirred at 60° C. for 5 hours, and thereafter, to the mixture, 5 M sodium hydroxide aqueous solution (5 mL) was added at room temperature and the mixture was extracted with ethyl acetate. The organic layer was dried, and thereafter, was concentrated to give the title compound (61.7 mg) having the following physical properties.

LC/MS $t_R$ 0.60 minutes: MS (ES$^+$) m/z 400 (M+H) (Condition b).

Example 4 (4): 2-[4-({[(2-methyl-2-propanyl)oxy]carbonyl}amino)phenyl]-2-oxoethyl (3S)-7-[2-(4-carbamoyl-1H-1,2,3-triazol-1-yl)-5-chlorophenyl]-5-oxo-1,2,3,5-tetrahydro-3-indolizinecarboxylate To a solution (61 mL) of the compound (6.10 g) prepared in Example 4 (3) in N,N-dimethylformamide, tert-butyl N-[4-(2-bromoacetyl)phenyl]carbamate (7.19 g) and N,N-diisopropylethylamine (5.3 mL) were added. The mixture was stirred at room temperature for 3 days, and thereafter, to the mixture, water and ethyl acetate were added. The precipitate was collected by filtration, and was washed with water, and thereafter, was dried to give the title compound (3.93 g) having the following physical properties.

LC/MS $t_R$ 0.90 minutes: MS (ES$^+$) m/z 633 (M+H) (Condition b).

Example 4 (5): 2-methyl-2-propanyl [4-(2-{(3S)-7-[2-(4-carbamoyl-1H-1,2,3-triazol-1-yl)-5-chlorophenyl]-5-oxo-1,2,3,5-tetrahydro-3-indolizinyl}-1H-imidazol-5-yl)phenyl]carbamate The compound (3.93 g) prepared in Example 4 (4) was dissolved in toluene (79 mL) and glacial acetic acid (3.9 mL), and to the mixture, ammonium acetate (9.57 g) was added. The mixture was stirred under reflux by heating for 4 hours, and thereafter, to the mixture, water and ethyl acetate were added. The organic layer was washed with water, and thereafter, was dried to give the title compound (3.98 g) having the following physical properties.

LC/MS $t_R$ 0.73 minutes: MS (ES$^+$) m/z 613 (M+H) (Condition b).

Example 4 (6): 2-methyl-2-propanyl [4-(2-{(3S)-7-[5-chloro-2-(4-cyano-1H-1,2,3-triazol-1-yl)phenyl]-5-oxo-1,2,3,5-tetrahydro-3-indolizinyl}-1H-imidazol-5-yl)phenyl]carbamate To a solution (76 mL) of the compound (3.81 g) prepared in Example 4 (5) in pyridine, trifluoroacetic anhydride (4.3 mL) was added with cooling (0° C.). The mixture was stirred at 0° C. for 2 hours, and thereafter, to the mixture, water was added, and the mixture was extracted with ethyl acetate. The organic layer was washed with saturated saline, and thereafter, was dried and was concentrated, and the obtained residue was dissolved in tetrahydrofuran, and to the mixture, aqueous ammonia was added, and the mixture was stirred for 30 minutes. The mixture was concentrated, and the residue was purified by column chromatography (diol silica gel, ethyl acetate:hexane=50:50 to 80:20) (aminosilica gel, ethyl acetate:hexane: 50:50 to 80:20) to give the title compound (2.39 g) having the following physical properties.

LC/MS $t_R$ 0.83 minutes: MS (ES+) m/z 595 (M+H) (Condition b).

Example 4 (7): 2-methyl-2-propanyl [4-(2-((3S)-7-[5-chloro-2-(4-cyano-1H-1,2,3-triazol-1-yl)phenyl]-5-oxo-1,2,3,5-tetrahydro-3-indolizinyl)-1-{[2-(trimethylsilyl)ethoxy]methyl}-1H-imidazol-4-yl)phenyl]carbamate To a solution (20 mL) of the compound (2.00 g) prepared in Example 4 (6) in N,N-dimethylformamide, N,N-diisopropylethylamine (0.87 mL) and 2-(trimethylsilyl)ethoxymethyl chloride (0.66 mL) were added with cooling (0° C.). The mixture was stirred at room temperature for 8 hours, and thereafter, to the mixture, saturated ammonium chloride aqueous solution was added, and the mixture was extracted with ethyl acetate. The organic layer was washed with saturated saline, and thereafter, was dried and was concentrated. The residue was purified by column chromatography (diol silica gel, ethyl acetate:hexane=30:70 to 50:50) to give the title compound (2.27 g) having the following physical properties.

LC/MS $t_R$ 1.17 minutes: MS (ES$^+$) m/z 725 (M+H) (Condition b).

Example 4 (8): 2-methyl-2-propanyl [4-(2-{(3S)-7-[5-chloro-2-(4-cyano-1H-1,2,3-triazol-1-yl)phenyl]-5-oxo-1,2,3,5-tetrahydro-3-indolizinyl}-5-fluoro-1-{[2-(trimethylsilyl)ethoxy)methyl}-1H-imidazol-4-yl)phenyl]carbamate The compound (560 mg) prepared in Example 4 (7) was dissolved in tetrahydrofuran (5.6 mL) and acetonitrile (2.8 mL), and to the mixture, sodium carbonate (205 mg) and 1-chloromethyl-4-fluoro-1,4-diazoniabicyclo[2.2.2]octane bis(tetrafluoroborate) (219 mg) were added at −10° C., and the mixture was stirred for 6 hours. The reaction mixture was diluted with ethyl acetate, and to the mixture, water was added, and the mixture was subjected to liquid separation, and the aqueous layer was extracted with ethyl acetate. The organic layers were combined, were washed with saturated saline, were dried, and thereafter, were concentrated. The residue was purified by column chromatography (ethyl acetate:hexane=30:70 to 50:50) to give the title compound (277 mg) having the following physical properties.

LC/MS $t_R$ 1.30 minutes: MS (ES$^+$) m/z 743 (M+H) (Condition a).

Example 4 (9): 2-methyl-2-propanyl [4-(2-{(3S)-7-[5-chloro-2-(4-cyano-1H-1,2,3-triazol-1-yl)phenyl]-5-oxo-1,2,3,5-tetrahydro-3-indolizinyl}-4-fluoro-1H-imidazol-5-yl)phenyl]carbamate To a solution (4.3 mL) of the compound (427 mg) prepared in Example 4 (8) in 1,4-dioxane, 5 M hydrochloric acid aqueous solution (0.43 mL) was added. The mixture was stirred at room temperature for 30 minutes, and thereafter, to the mixture, saturated sodium bicarbonate aqueous solution was added, and the mixture was extracted with ethyl acetate. The organic layer was washed with saturated saline, and thereafter, was dried and was concentrated. The residue was purified by column chromatography (diol silica gel, ethyl acetate:hexane=35:65 to 50:50) to give the title compound (320 mg) having the following physical properties.

LC/MS $t_R$ 1.11 minutes: MS (ES$^+$) m/z 613 (M+H) (Condition a).

Example 4 (10): 1-(2-{(3S)-3-[5-(4-aminophenyl)-4-fluoro-1H-imidazol-2-yl]-5-oxo-1,2,3,5-tetrahydro-7-indolizinyl}-4-chlorophenyl)-1H-1,2,3-triazole-4-carbonitrile

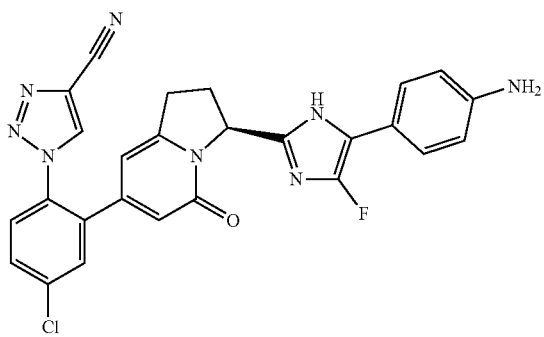 [SMILES: N#Cc1cn(-c2ccc(Cl)cc2-c2cc3n(c(=O)c2)[C@H](c2nc(F)c(-c4ccc(N)cc4)[nH]2)CC3)nn1]

To a solution (6.4 mL) of the compound (320 mg) prepared in Example 4 (9) in dichloromethane, trifluoroacetic acid (0.96 mL) was added. The mixture was stirred at room temperature for 45 minutes, and thereafter, to the mixture, toluene was added and the mixture was concentrated. The residue was purified by column chromatography (aminosilica gel, ethyl acetate:hexane=65:35 to 100:0) to give the title compound (232 mg) having the following physical properties.

LC/MS $t_R$ 0.79 minutes: MS (ES$^+$) m/z 513 (M+H) (Condition a);

$^1$H NMR (300 MHz, methanol-$d_4$); δ 8.88 (s, 1H), 7.73-7.65 (m, 3H), 7.30 (d, 2H), 6.75 (d, 2H), 6.11 (s, 1H), 6.08 (s, 1H), 5.70 (d, 1H), 3.42 (m, 1H), 3.10 (m, 1H), 2.61 (m, 1H), 2.39 (m, 1H).

Biological Experimental Examples will be described hereinbelow, and the effects of the compound of the present invention were confirmed based on the experimental methods.

Meanwhile, as Comparative Compounds, the following compounds described in Patent Literature 6 were used. With regard to the Biological Experimental Examples hereinbelow, the Comparative Compounds were evaluated in the same manner as the compound of the present invention.

(3S)-3-[5-(6-amino-2-fluoro-3-pyridinyl)-1H-imidazol-2-yl]-7-[5-chloro-2-(1H-tetrazol-1-yl)phenyl]-2,3-dihydro-5(1H)-indolizinone (referred to as Comparative Example 1 (1)):

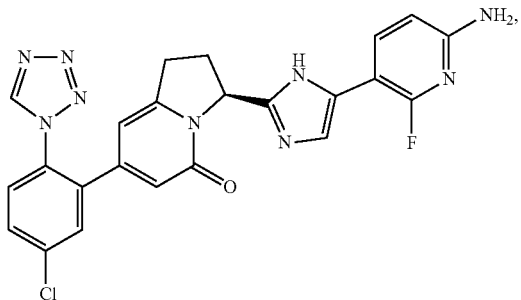 [SMILES: Nc1ccc(-c2cnc([C@@H]3CCc4cc(-c5cc(Cl)ccc5-n5cnnn5)cc(=O)n43)[nH]2)c(F)n1]

(3S)-3-[5-(6-amino-2-fluoro-3-pyridinyl)-4-chloro-1H-imidazol-2-yl]-7-[5-chloro-2-(1H-tetrazol-1-yl)phenyl]-2,3-dihydro-5(1H)-indolizinone (referred to as Comparative Example 1 (2)):

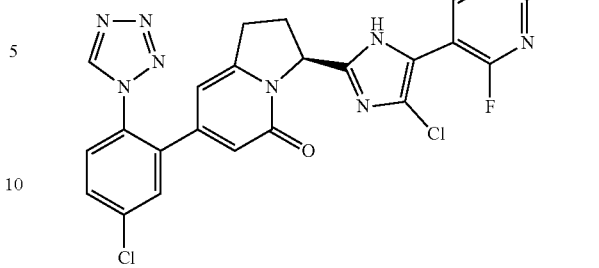

(3S)-3-[5-(6-amino-3-pyridinyl)-4-fluoro-1H-imidazol-2-yl]-7-[5-chloro-2-(1H-tetrazol-1-yl)phenyl]-2,3-dihydro-5(1H)-indolizinone (referred to as Comparative Example 1 (3)):

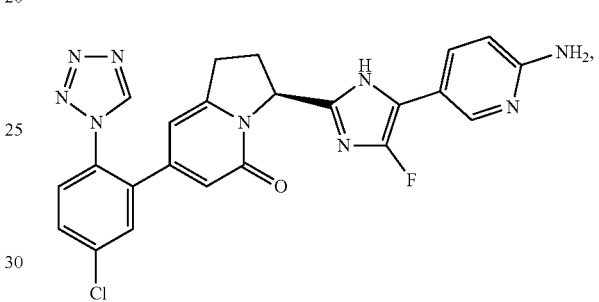

(3S)-3-[2-(6-amino-2-fluoro-3-pyridinyl)-1H-imidazol-5-yl]-7-[5-chloro-2-(1H-tetrazol-1-yl)phenyl]-2,3-dihydro-5(1H)-indolizinone (Comparative Example 2 (1)):

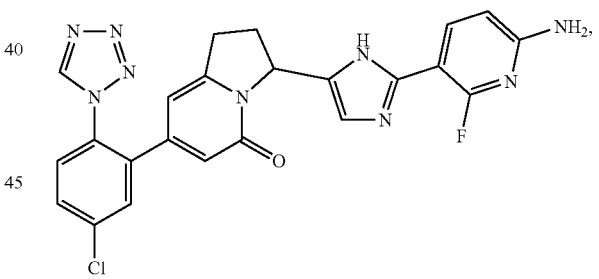

(3S)-3-[2-(6-amino-2-fluoro-3-pyridinyl)-4-chloro-1H-imidazol-5-yl]-7-[5-chloro-2-(1H-tetrazol-1-yl)phenyl]-2,3-dihydro-5(1H)-indolizinone (Comparative Example 2 (3)):

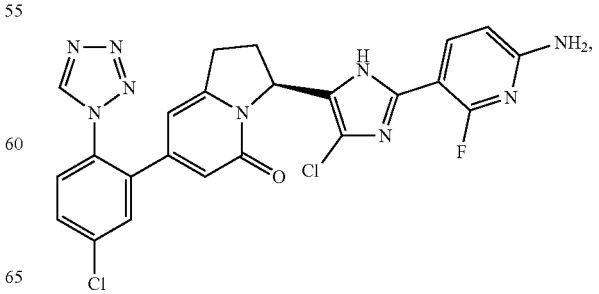

(3S)-3-[2-(6-amino-3-pyridinyl)-4-fluoro-1H-imidazol-5-yl]-7-[5-chloro-2-(1H-tetrazol-1-yl)phenyl]-2,3-dihydro-5(1H)-indolizinone (Comparative Example 2 (5)):

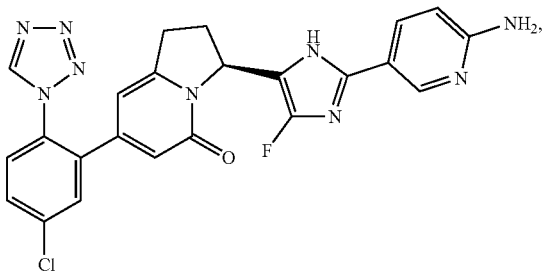 [SMILES: Nc1ccc(-c2nc(F)c([C@@H]3CCc4cc(-c5cc(Cl)ccc5-n5cnnn5)cc(=O)n43)[nH]2)cn1]

methyl [4-(4-chloro-5-{(6S)-2-[5-chloro-2-(1H-tetrazol-1-yl)phenyl]-4-oxo-4,6,7,8-tetrahydropyrrolo[1,2-a]pyrimidin-6-yl}-1H-imidazol-2-yl)phenyl]carbamate (Comparative Example 3 (1)):

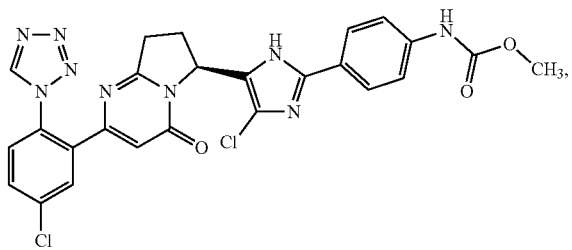 [SMILES: COC(=O)Nc1ccc(-c2nc(Cl)c([C@@H]3CCc4nc(-c5cc(Cl)ccc5-n5cnnn5)cc(=O)n43)[nH]2)cc1]

(6S)-6-[5-(6-amino-2-fluoro-3-pyridinyl)-4-chloro-1H-imidazol-2-yl]-2-[5-chloro-2-(1H-tetrazol-1-yl)phenyl]-7,8-dihydropyrrolo[1,2-a]pyrimidin-4(6H)-one (Comparative Example 3 (2)):

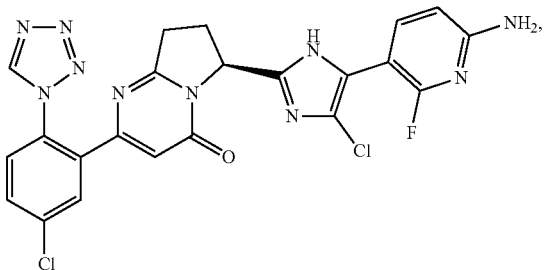 [SMILES: Nc1ccc(-c2[nH]c([C@@H]3CCc4nc(-c5cc(Cl)ccc5-n5cnnn5)cc(=O)n43)nc2Cl)c(F)n1]

1-(2-{(3S)-3-[5-(6-amino-3-pyridinyl)-4-chloro-1H-imidazol-2-yl]-5-oxo-1,2,3,5-tetrahydro-7-indolizinyl}-4-chlorophenyl)-1H-1,2,3-triazole-4-carbonitrile (referred to as Comparative Example 4):

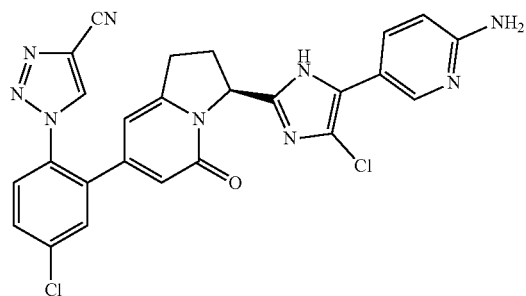 [SMILES: N#Cc1cn(-c2ccc(Cl)cc2-c2cc3n(c(=O)c2)[C@H](c2nc(Cl)c(-c4ccc(N)nc4)[nH]2)CC3)nn1]

Biological Example 1

(1) In Vitro Assay

Inhibitory activities of the compound of the present invention on human blood coagulation factor XIa, factor VIIa, factor IXa, factor Xa, factor XIIa, plasma kallikrein and thrombin were evaluated. A chromogenic substrate solution was added to each of enzyme solutions, the absorbance at 405 nm was measured continuously at 37° C. for 5 minutes at intervals of 15 seconds, and the decomposition rate of each of substrates (mOD/min) was calculated. The half maximal (50%) inhibitory concentration (IC50) of the compound of the present invention on each of the enzymes was calculated by linear regression by using least-squares method from the concentration of the compound of the present invention which was converted in terms of natural logarithm and the rate of enzyme inhibition calculated according to the following equation.

The rate of enzyme inhibition (%) of the compound of the present invention was calculated by using the following equation:

Rate of enzyme inhibition (%)=100×{(Cont($e$)−BL($e$))−(Comp($e$)−BL($e$))/(Cont($e$)−BL($e$))}

Cont (e): Decomposition rate of substrate (mOD/min) when enzyme solution and substrate solution were added to physiological saline containing 5% dimethyl sulfoxide BL (e): Decomposition rate of substrate (mOD/min) when buffer solution which did not contain enzyme and substrate solution were added to physiological saline containing 5% dimethyl sulfoxide Comp (e): Decomposition rate of substrate (mOD/min) when enzyme solution and substrate solution were added to physiological saline containing 5% dimethyl sulfoxide and the compound of the present invention (1-1) Measurement of Inhibitory Activity on Human Blood Coagulation Factor XIa:

The inhibitory activity on human blood coagulation factor XIa (Haematologic Technologies Inc.) was measured by using the enzyme solution adjusted to 0.1 U/mL by a buffer solution containing 300 mM of NaCl, 10 mM of KCl, 2 mg/mL of PEG 6000 and 100 mM of HEPES-NaOH (pH 7.4) as well as S-2366 (pyroglu-Pro-Arg-pNA, CHROMOGENIX) adjusted to 1 mM by distilled water.

(1-2) Measurement of Inhibitory Activity on Human Plasma Kallikrein:

The inhibitory activity on human plasma kallikrein (Enzyme Research Laboratories Ltd.) was measured by using the enzyme solution adjusted to 20 mU/mL by a buffer solution containing 400 mM of NaCl, 10 mg/mL of PEG 6000 and 200 mM of phosphate buffer solution (pH 7.4) as well as S-2302 (H-D-Pro-Phe-Arg-pNA, CHROMOGENIX) adjusted to 500 µM by distilled water.

(1-3) Measurement of Inhibitory Activities on Human Blood Coagulation Factor Xa and Human Thrombin:

The inhibitory activity on human blood coagulation factor Xa (Sekisui Diagnostics LLC.) and the inhibitory activity on human thrombin (Sigma) were measured by using each of the enzyme solutions adjusted to 0.5 U/mL or 0.25 U/mL, respectively, by a buffer solution containing 300 mM of NaCl, 4 mg/mL of PEG 6000 and 100 mM of Tris-HCl (pH 7.4) as well as S-2222 (Bz-Ile-Glu(γ-OR)-Gly-Arg-pNA.HCl, R=H (50%) and R=CH3 (50%), CHROMOGENIX) or S-2366 each adjusted to 1 mM by distilled water.

(1-4) Measurement of Inhibitory Activity on Human Blood Coagulation Factor XIIa:

The inhibitory activity on human blood coagulation factor XIIa (Enzyme Research Laboratories Ltd.) was measured by using the enzyme solution adjusted to 0.78 U/mL by a buffer solution containing 300 mM of NaCl and 100 mM of Tris-HCl (pH 7.4) as well as S-2302 adjusted to 1 mM by distilled water.

(1-5) Inhibitory Activity on Human Blood Coagulation Factor IXa:

The inhibitory activity on human blood coagulation factor IXa (Sekisui Diagnostics LLC.) was measured by using the enzyme solution adjusted to 30 U/mL by a buffer solution containing 200 mM of NaCl, 10 mM of $CaCl_2$, 60% of ethylene glycol and 100 mM of Tris-HCl (pH 7.4) as well as Spectrozume FIXa (H-D-Leu-Ph'Gly-Arg-pNA.2AcOH, Sekisui Diagnostics LLC.) adjusted to 10 mM by distilled water.

(1-6) Inhibitory Activity on Human Blood Coagulation Factor VIIa:

The inhibitory activity on human blood coagulation factor VIIa (Sekisui Diagnostics LLC.) was measured by using the enzyme solution adjusted to 200 U/mL by a buffer solution containing 300 mM of NaCl, 10 mM of $CaCl_2$, 10 mg/mL of PEG 6000, 100 mM of HEPES-NaOH (pH 7.4) and recombinant human tissue factor (prepared according to the method of Alireza R. Rezaie et al., (Protein expression and purification, 1992, Vol. 3, No. 6, pages 453-460)) as well as S-2288 (H-D-Ile-Pro-Arg-pNA, CHROMOGENIX) adjusted to 10 mM by distilled water.

(2) Measurement of Activated Partial Thromboplastin Time and Prothrombin Time

Activated partial thromboplastin time (APTT) and prothrombin time (PT) were measured by using a fully automatic device for measuring blood coagulation (CA-1500, Sysmex Corporation). On APTT or PT measurement, standard human plasma for the blood coagulation tests (Siemens Healthcare Diagnostics GmbH) was mixed with a diluted solution of the compound of the present invention, and thereafter, APTT reagent (Siemens Healthcare Diagnostics GmbH) and 0.02 M of calcium chloride or PT reagent (Siemens Healthcare Diagnostics GmbH) were automatically added to the mixture in order to initiate clot formation. The anticoagulation activity (APTT×2 or PT×2) of the compound of the present invention was expressed as a concentration required for doubling the coagulation time in the vehicle (1% DMSO) group. APTT×2 or PT×2 was determined by plotting the concentration of the compound of the present invention against a twofold increase in the coagulation time.

TABLE 1

|  | FXIa inhibitory activity IC50 (µM) | APTT × (µM) |
|---|---|---|
| Example 1 (6) | 0.0017 | 0.80 |
| Example 2 (10) | 0.0017 | 0.49 |
| Example 3 (4) | 0.0019 | 0.47 |
| Example 4 (10) | 0.0054 | 1.8 |
| Comparative Example 1 (1) | 0.0038 | 1.2 |
| Comparative Example 1 (2) | 0.0048 | 1.8 |
| Comparative Example 1 (3) | 0.0014 | 0.55 |
| Comparative Example 2 (1) | 0.019 | 4.0 |
| Comparative Example 2 (3) | 0.0044 | 2.1 |
| Comparative Example 2 (5) | 0.0016 | 0.21 |
| Comparative Example 3 (1) | 0.0016 | 0.64 |
| Comparative Example 3 (2) | 0.011 | 3.7 |
| Comparative Example 4 | 0.0027 | 2.0 |

As a result of the above-described tests, it was confirmed that the compound of the present invention has a potent FXIa inhibitory activity and an anticoagulation activity. Meanwhile, inhibitory activities of the compound of the present invention on human blood coagulation factor Xa, factor XIIa, factor IXa, factor VIIa and human thrombin were sufficiently low.

Biological Experimental Example 2:
Pharmacokinetic (PK) Tests in Rats

The compound of the present invention was administered to fasted male Crj:CD(SD) rats by intravenous injection as a single intravenous dose of 0.1 mg/kg (vehicle: 20% HP-β-CD solution) and by forced oral dosage as a dose of 1 mg/kg per os (vehicle: 0.5% methylcellulose solution). Blood samples were collected from cervical vein into heparinized syringes at 0.08, 0.25, 0.5, 1, 3 or 7 hours after administration by intravenous injection or 0.08, 0.25, 0.5, 1, 2, 4, 6, 8 or 24 hours after oral administration. Plasma was obtained by centrifugation, and plasma was stored at −20° C. until measurement of plasma concentration.

In order to measure the plasma concentration of the compound of the present invention, the plasma sample was subjected to deproteinization by using acetonitrile, was filtrated by using a filter, and thereafter, was diluted with purified water, and then was analyzed by LC/MS/MS. A column for analysis (Shim-pack XR-ODSII, 2.0 mm×75 mm, 2.2 µm) and mobile phases (0.1% formic acid in water and 0.1% formic acid in acetonitrile, flow rate: 0.5 mL/min) were used. The system was used by detection of cations in the Multiple Reaction Monitoring (MRM) mode.

The area under the blood concentration versus time curve (AUC) and the bioavailability (BA) of the compound of the present invention were calculated. In addition, as indices of the maintaining time of the anticoagulation activity in the case of oral administration, AUC/APTT×2, which is obtained by dividing AUC by APTT×2, and C8h/APTT×2, which is obtained by dividing C8h (the plasma concentration at 8 hours after administration) by APTT×2, were calculated.

TABLE 2

|  | AUC (µM · h) | Plasma concentration C8h (µM) | AUC/ APTT × 2 | C8h/ APTT × 2 |
|---|---|---|---|---|
| Example 1 (6) | 33 | 0.88 | 41 | 1.1 |
| Example 2 (10) | 15 | 1.0 | 30 | 2.1 |
| Example 3 (4) | 28 | 1.6 | 61 | 3.4 |
| Example 4 (10) | 45 | 2.5 | 25 | 1.4 |
| Comparative Example 1 (1) | 4.7 | 0.17 | 4.0 | 0.15 |
| Comparative Example 1 (2) | 0.69 | 0.026 | 0.39 | 0.014 |
| Comparative Example 1 (3) | 1.7 | 0.081 | 3.0 | 0.15 |
| Comparative Example 2 (1) | 0.056 | BLQ* | 0.014 | — |
| Comparative Example 2 (3) | 23 | 1.1 | 11 | 0.52 |
| Comparative Example 2 (5) | 1.6 | 0.073 | 7.5 | 0.34 |
| Comparative Example 3 (1) | 4.2 | 0.18 | 6.5 | 0.29 |
| Comparative Example 3 (2) | 1.4 | 0.027 | 0.39 | 0.0073 |
| Comparative Example 4 | 8.4 | 0.35 | 4.2 | 0.18 |

*BLQ: Below the Limit of Quantitation (0.0024 µM)

In addition, the period of time when the compound concentration in plasma of the compound of the present invention exceeded APTT×2 (the APTT×2 maintaining time) was calculated from the change in the compound concentration in plasma in the case when the compound of the present invention was orally administered at a dose of 1 mg/kg. The longer the APTT×2 maintaining time is, the longer the period of time is when the anticoagulation activity is maintained after oral administration. Accordingly, it is suggested that a compound which exhibits a long APTT×2 maintaining time may be an excellent agent for preventing and/or treating thromboembolic disease which requires a small number of administrations.

TABLE 3

|  | APTT × 2 maintaining time (h) |
|---|---|
| Example 1 (6) | >8 |
| Example 2 (10) | >8 |
| Example 3 (4) | >8 |
| Example 4 (10) | >8 |
| Comparative Example 1 (1) | 0* |
| Comparative Example 1 (2) | 0* |
| Comparative Example 1 (3) | <1 |
| Comparative Example 2 (1) | 0* |
| Comparative Example 2 (3) | <2 |
| Comparative Example 2 (5) | <2 |
| Comparative Example 3 (1) | <2 |
| Comparative Example 3 (2) | 0* |
| Comparative Example 4 | 0* |

*Plasma concentration at any time point of blood collection did not exceed APTT × 2 (μm).

Figure 2:
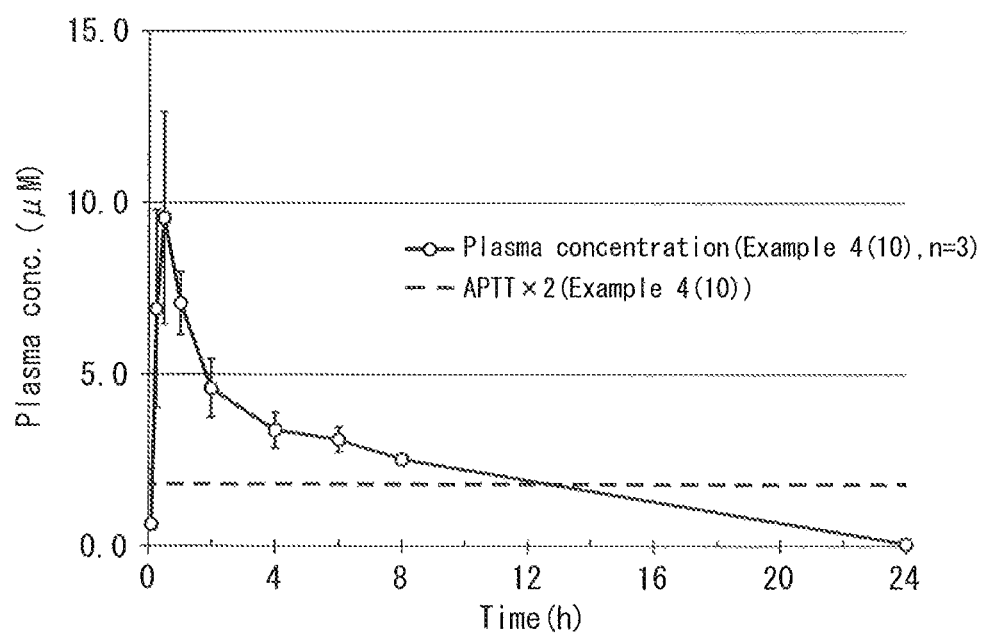
FIG. 2 shows the change in the concentration of the compound in the plasma of the compound described in Example 4 (10) when being orally administered to rats (1 mg/kg) and the relationship to APTT×2 in an in vitro assay. The longitudinal axis shows the concentration of the compound in the plasma and the horizontal axis shows time after oral administration.
Figure 3:
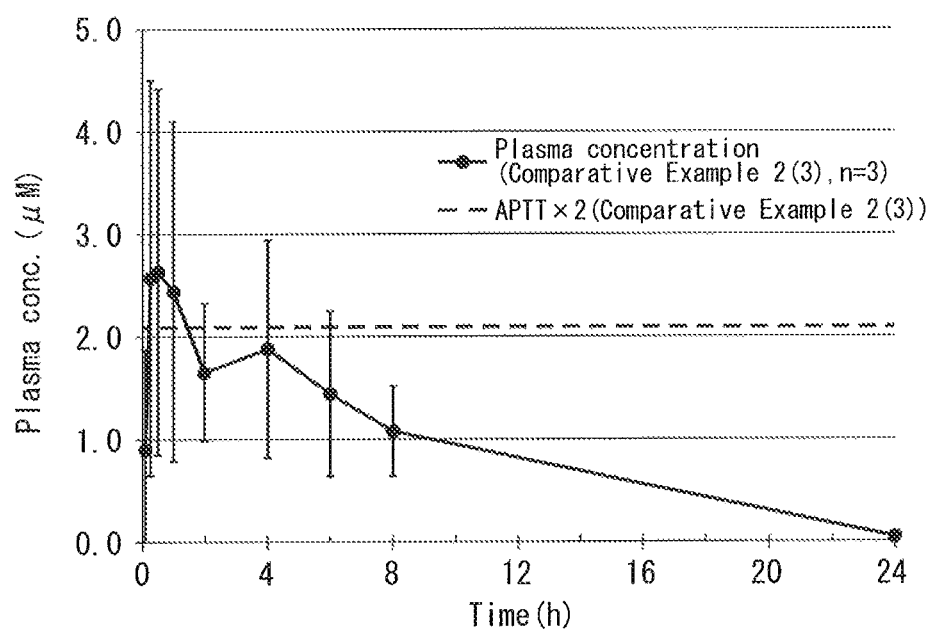
FIG. 3 shows the change in the concentration of the compound in the plasma of the compound described in Comparative Example 2 (3) when being orally administered to rats (1 mg/kg) and the relationship to APTT×2 in an in vitro assay. The longitudinal axis shows the concentration of the compound in the plasma and the horizontal axis shows time after oral administration.

In addition, the relationships of the changes in the compound concentrations in plasma of the compounds described in Example 2 (10), Example 4 (10) and Comparative Example 2 (3) with APTT×2 are shown in FIG. 1, FIG. 2 and FIG. 3.

As a result of the above-described tests, it was confirmed that the compound of the present invention exhibited good kinetics in blood. In addition, when the compound of the present invention was orally administered at a dose of 1 mg/kg, the compound of the present invention showed a C8h/APTT×2 of equal to or more than 1. Further, while the compound of the present invention maintained the plasma concentration equal to or higher than APTT×2 for 8 hours or longer, the APTT×2 maintaining time of each of Comparative Compounds was shorter than 2 hours.

From the results described above, it was confirmed that the compound of the present invention exhibited both good kinetics in blood and a potent anticoagulation activity and is capable of exhibiting the anticoagulation activity for a long period of time after oral administration.

Biological Experimental Example 3: Drug Interaction (1) CYP Inhibitory Activity
Competitive Inhibitory Activity
Midazolam and the compound of the present invention were added to a suspension of human liver microsomes and the mixture was shaken at 37° C. for 3 minutes, and thereafter, the concentration of 1'-hydroxymidazolam in the sample was analyzed by LC/MS/MS.
Time-Dependent Inhibitory (TDI) Activity
The compound of the present invention was added to a suspension of human liver microsomes and the mixture was shaken at 37° C. for 30 minutes, and thereafter, midazolam was added to the mixture, and the mixture was further shaken for 3 minutes. The concentration of 1'-hydroxymidazolam in the sample after shaking was analyzed by LC/MS/MS.

With regard to both the competitive inhibitory activity and the TDI activity, a column for analysis (Shim-pack XR-ODSII, 2.0 mm×75 mm, 2.2 μm) and mobile phases (0.1% formic acid in water and 0.1% formic acid in acetonitrile, flow rate: 0.5 mL/min) were used. The system was used by detection of cations in the Multiple Reaction Monitoring (MRM) mode. As an index of the CYP inhibitory activity of the competitive inhibition and TDI, the IC50 value was calculated according to the following equations by using a plurality of the concentrations of the compound of the present invention in the sample selected from 1, 3, 10, 15, 30 and 50 μmol/L. However, when the inhibition rate was equal to or higher than 50% in the case where each of the compounds was evaluated at the minimum concentration of 1 or 5 μmol/L, the IC50 value was evaluated as <1 or <5 μmol/L, and when the inhibition rate was equal to or lower than 50% in the case where each of the compounds was evaluated at the maximum concentration of 10, 30 or 50 μmol/L, the IC50 value was evaluated as >10, >30 or >50 μmol/L, respectively.

$$IC50 = (50-a)/b$$

$$a = (B \times C - D \times A)/(B-D)$$

$$b = (A-C)/(B-D)$$

Inhibition rate (%)=100−(the concentration of 1'-hydroxymidazolam at the time when the compound of the present invention was added)/(the concentration of 1'-hydroxymidazolam at the time when the compound of the present invention was not added)×100

The lowest inhibition rate which exceeded the inhibition rate 50% was taken to be A (%), and the concentration of the compound of the present invention at that time was taken to be B (μmol/L). On the other hand, the highest inhibition rate which was lower than the inhibition rate 50% was taken to be C (%), and the concentration of the compound of the present invention at that time was taken to be D (μmol/L).

In addition, as an index of the discrepancy between the concentration at which the anticoagulation activity can be exhibited and the CYP inhibitory activity, the CYP IC50 value (TDI)/APTT×2 was calculated.

TABLE 4

|  | CYP IC50 (μM) | CYP IC50 (TDI) (μM) | CYP IC50 (TDI)/ APTT × 2 |
|---|---|---|---|
| Example 1 (6) | 28 | 3.8 | 4.8 |
| Example 2 (10) | >50 | 31 | 64 |
| Example 3 (4) | 18 | 14 | 31 |
| Example 4 (10) | 9.1 | 5.0 | 2.8 |

As a result of the above-described tests, it was confirmed that the CYP inhibitory activity of the compound of the present invention was low. In addition, it was confirmed that there was a discrepancy between the anticoagulation activity and the CYP inhibitory activity.

From the above-described results, it was confirmed that the compound of the present invention is a compound which is a potent FXIa inhibitor, is excellent in oral absorbability and kinetics in blood, exhibits a potent anticoagulation activity for a long period of time after oral administration and exhibits a discrepancy between the anticoagulation activity and the CYP inhibitory activity.

(2) Evaluation of CYP3A4 Inhibition by Using Hepatic Cells Suspended in Serum

The compound of the present invention was added to a suspension of human hepatic cells suspended in human serum and the mixture was shaken at 37° C. for 10 minutes. Thereafter, midazolam was added to the mixture and the mixture was further shaken for 90 minutes. The concentration of 1'-hydroxymidazolam in the sample after shaking was analyzed by LC/MS/MS. A column for analysis (Shimpack XR-ODSII, 2.0 mm×75 mm, 2.2 μm) and mobile phases (0.1% formic acid in water and 0.1% formic acid in acetonitrile, flow rate: 0.5 mL/min) were used. The system was used by detection of cations in the Multiple Reaction Monitoring (MRM) mode. The concentration of the compound of the present invention in the sample was made to be 10 μmol/L, 30 μmol/L or 100 μmol/L.

Biological Experimental Example 4: Toxicity (1) hERG Inhibitory Action

The hERG inhibitory activity of the compound of the present invention was measured by the following procedure.

The hERG channel current (IKr) induced by stimulation pulses was measured by using CHO-K1 cells transfected with hERG gene and using a fully automatic patch clamp system according to the amphotericin-perforated patch clamp technique. The stimulation pulses were set as follows: holding potential: −80 mV, depolarizing potential: +40 mV (2 seconds) and repolarizing potential: −50 mV (2 seconds). The maximum tail current induced after applying the repolarizing potential was measured. Stimulation pulses were applied twice, that is, before adding the compound of the present invention and 5 minutes after adding the compound of the present invention. The rate of change of the maximum tail current to the current before adding the compound of the present invention was calculated. The compound of the present invention was used as a solution in dimethyl sulfoxide (DMSO) and was added at the concentration of 1% to the extracellular fluid. The inhibition rate (%) of the hERG channel was calculated by correcting the rate of change in the maximum tail current before and after the addition of the compound of the present invention by the rate of change in a vehicle-treated group.

Inhibition rate (%)=[1−(the rate of change in current before and after the addition of the compound of the present invention)/(the rate of change in current before and after the addition of the vehicle)]×100

As a result, when the compound of the present invention was added to cells at the concentration of 10 μM, the hERG inhibition rate was below 51%. From the above-described result, it could be confirmed that the compound of the present invention has a low hERG inhibitory activity, and therefore, is a compound excellent in safety.

(2) Evaluation of Steatosis

The steatosis-inducing effect of the compound of the present invention was measured by the following procedure.

To a medium of a human immortalized hepatic cell line Fa2N-4, 1% of a solution of the compound of the present invention in DMSO at a concentration of 6.25, 12.5, 25, 50 or 100 μM was added, and the cells were exposed for 72 hours. Thereafter, Nile Red was added to the medium, and the fluorescence intensity of the cells was measured at an excitation wavelength of 485 nm and an fluorescent wavelength of 570 nm. When the measured fluorescence value was equal to or more than 160% of the value obtained by a vehicle treatment, it was determined that the compound exhibits a steatosis-inducing effect.

As a result, when the concentration of the compound of the present invention in the medium was 25 μM, the measured fluorescence value was less than 160% of the measured fluorescence value in the case of the vehicle treatment. From the above-described result, it could be confirmed that the compound of the present invention exhibits a low steatosis-inducing effect and is a compound excellent in safety.

Preparation Examples

Preparation Example 1

The following ingredients are mixed in a conventional manner and compressed to give 10,000 tablets each containing 10 mg of the active ingredient.

| | |
|---|---|
| (3S)-3-[5-(6-amino-2-fluoro-3-pyridinyl)-4-fluoro-1H-imidazol-2-yl]-7-[5-chloro-2-(1H-tetrazol-1-yl)phenyl]-2,3-dihydro-5(1H)-indolizinone | 100 g |
| Carboxymethyl cellulose calcium | 20 g |
| Magnesium stearate | 10 g |
| Microcrystalline cellulose | 870 g |

Preparation Example 2

The following ingredients are mixed in a conventional manner. Thereafter, the mixture is filtered through a dust filter, and 5 ml aliquots are charged into ampules. The ampules are heat sterilized by an autoclave to give 10,000 ampules each containing 20 mg of the active ingredient.

| | |
|---|---|
| (3S)-3-[5-(6-amino-2-fluoro-3-pyridinyl)-4-fluoro-1H-imidazol-2-yl]-7-[5-chloro-2-(1H-tetrazol-1-yl)phenyl]-2,3-dihydro-5(1H)-indolizinone | 200 g |
| Mannitol | 20 g |
| Distilled water | 50 L |

INDUSTRIAL APPLICABILITY

The compound of the present invention has a potent FXIa inhibitory activity, and therefore, is useful for the prevention and/or treatment of thromboembolic disease.

The invention claimed is:

1. A method for treating thromboembolic disease, comprising administering an effective dose of (3S)-3-[2-(6-amino-2-fluoro-3-pyridinyl)-4-fluoro-1H-imidazol-5-yl]-7-[5-chloro-2-(1H-tetrazol-1-yl)phenyl]-2,3-dihydro-5(1H)-indolizinone to a patient in need of treatment of the thromboembolic disease.

2. The method according to claim 1, wherein the thromboembolic disease is arterial cardiovascular thromboembolic disorder, venous cardiovascular thromboembolic disorder, arterial cerebrovascular thromboembolic disorder, venous cerebrovascular thromboembolic disorder or thromboembolic disorder in the heart chamber or in the peripheral circulation.

3. The method according to claim 1, wherein the thromboembolic disease is coronary artery disease, unstable angina, acute coronary syndrome, atrial fibrillation, myocardial infarction, ischemic sudden death, transient ischemic attack, cerebral stroke, peripheral arterial disease, atherosclerosis, peripheral occlusive arterial disease, venous thrombosis, venous thromboembolism, deep venous thrombosis, thrombophlebitis, arterial embolism, coronary artery thrombosis, cerebral arterial thrombosis, cerebral embolism, kidney embolism, portal vein thrombosis, pulmonary embolism, pulmonary infarction, liver embolism, hepatic veno-occlusive disease/sinusoidal obstruction syndrome, thrombotic microangiopathy, disseminated intravascular coagulation, sepsis, acute respiratory distress syndrome, acute lung injury, antiphospholipid antibody syndrome, thrombosis resulting from coronary artery bypass graft surgery or thrombosis induced by treatment in which blood is exposed to an artificial surface which promotes thrombus formation.

4. The method according to claim 1, wherein the thromboembolic disease is venous thromboembolism, ischemic stroke, thromboembolic disease induced by treatment in which blood is exposed to an artificial surface which promotes thrombus formation, acute coronary syndrome, coronary artery disease or peripheral arterial disease.

* * * * *

UNITED STATES PATENT AND TRADEMARK OFFICE
CERTIFICATE OF CORRECTION

PATENT NO. : 10,815,233 B2
APPLICATION NO. : 16/720486
DATED : October 27, 2020
INVENTOR(S) : Motoyuki Tanaka et al.

Page 1 of 1

It is certified that error appears in the above-identified patent and that said Letters Patent is hereby corrected as shown below:

On the Title Page

Column 1, item (60), Related U.S. Application Data, Line 1, Delete "(60)" and insert --(62)--

Column 2, item (56), Other Publications, Line 13, after "Refusal", delete "translation"

Signed and Sealed this
Second Day of February, 2021

Drew Hirshfeld
*Performing the Functions and Duties of the*
*Under Secretary of Commerce for Intellectual Property and*
*Director of the United States Patent and Trademark Office*